US012673044B2

(12) United States Patent
Buesa Arjol et al.

(10) Patent No.: US 12,673,044 B2
(45) Date of Patent: Jul. 7, 2026

(54) METHODS OF TREATING BORDERLINE PERSONALITY DISORDER

(71) Applicant: ORYZON GENOMICS, S.A., Madrid (ES)

(72) Inventors: Carlos Manuel Buesa Arjol, Castelldefels (ES); Roger Alan Bullock, Portimao (PT); José Antonio Ramos Quiroga, Barcelona (ES)

(73) Assignee: ORYZON GENOMICS, S.A., Madrid (ES)

( * ) Notice: Subject to any disclaimer, the term of this patent is extended or adjusted under 35 U.S.C. 154(b) by 1095 days.

(21) Appl. No.: 17/439,575

(22) PCT Filed: Mar. 20, 2020

(86) PCT No.: PCT/EP2020/057803

§ 371 (c)(1),
(2) Date: Sep. 15, 2021

(87) PCT Pub. No.: WO2020/188090

PCT Pub. Date: Sep. 24, 2020

(65) Prior Publication Data

US 2022/0151998 A1 May 19, 2022

(30) Foreign Application Priority Data

Mar. 20, 2019 (EP) .................................... 19382196

(51) Int. Cl.
*A61K 31/4245* (2006.01)
*A61P 25/18* (2006.01)

(52) U.S. Cl.
CPC .......... *A61K 31/4245* (2013.01); *A61P 25/18* (2018.01)

(58) Field of Classification Search
None
See application file for complete search history.

(56) References Cited

U.S. PATENT DOCUMENTS

| | | | |
|---|---|---|---|
| 8,524,717 | B2 | 9/2013 | Guibourt et al. |
| 8,722,743 | B2 | 5/2014 | Ortega Munoz et al. |
| 8,859,555 | B2 | 10/2014 | Ortega Munoz et al. |
| 8,946,296 | B2 | 2/2015 | Ortega Munoz et al. |
| 8,993,808 | B2 | 3/2015 | Guibourt et al. |
| 9,006,449 | B2 | 4/2015 | Fyfe et al. |
| 9,061,966 | B2 | 6/2015 | Laria et al. |
| 9,149,447 | B2 | 10/2015 | Muñoz et al. |
| 9,181,198 | B2 | 11/2015 | Ortega Muñoz et al. |
| 9,186,337 | B2 | 11/2015 | Baker et al. |
| 9,469,597 | B2 | 10/2016 | Ortega Muñoz et al. |
| 9,487,512 | B2 | 11/2016 | Ortega Muñoz et al. |
| 9,616,058 | B2 | 4/2017 | Cesar Castro Palomino Laria et al. |
| 9,670,136 | B2 | 6/2017 | Ortega Muñoz et al. |
| 9,676,701 | B2 | 6/2017 | Fyfe et al. |
| 9,708,309 | B2 | 7/2017 | Ortega Muñoz et al. |
| 9,790,196 | B2 | 10/2017 | Baker et al. |
| 9,908,859 | B2 | 3/2018 | Baker et al. |
| 9,944,601 | B2 | 4/2018 | Ortega Muñoz et al. |
| 10,202,330 | B2 | 2/2019 | Muñoz et al. |
| 10,214,477 | B2 | 2/2019 | Ortega Muñoz et al. |
| 10,221,125 | B2 | 3/2019 | Diodone et al. |
| 10,233,178 | B2 | 3/2019 | Ortega Muñoz et al. |
| 10,265,279 | B2 | 4/2019 | Demario et al. |
| 10,329,256 | B2 | 6/2019 | Ortega Muñoz et al. |
| 10,780,081 | B2 | 9/2020 | Maes et al. |
| 11,013,698 | B2 | 5/2021 | Ciceri et al. |
| 11,034,991 | B2 | 6/2021 | Carceller González et al. |
| 2013/0303545 | A1 | 11/2013 | Maes et al. |
| 2014/0163041 | A1 | 6/2014 | Fyfe et al. |
| 2014/0296255 | A1 | 10/2014 | Maes et al. |
| 2014/0329833 | A1 | 11/2014 | Maes et al. |
| 2016/0000768 | A1 | 1/2016 | Castro-Palomino Laria et al. |
| 2016/0045456 | A1 | 2/2016 | Guibourt et al. |
| 2016/0081947 | A1 | 3/2016 | Maes et al. |
| 2017/0209432 | A1 | 7/2017 | Fyfe et al. |
| 2017/0281566 | A1 | 10/2017 | Ciceri et al. |
| 2018/0284095 | A1 | 10/2018 | Maes et al. |
| 2019/0153538 | A1 | 5/2019 | Cheng et al. |
| 2019/0256929 | A1 | 8/2019 | Birzele et al. |
| 2019/0256930 | A1 | 8/2019 | Arévalo Sánchez et al. |
| 2020/0323828 | A1 | 10/2020 | Maes et al. |
| 2021/0228490 | A1 | 7/2021 | Maurer et al. |
| 2022/0151999 | A1 | 5/2022 | Buesa Arjol et al. |
| 2022/0175698 | A1 | 6/2022 | Ciceri |
| 2022/0331265 | A1 | 10/2022 | Ciceri et al. |
| 2022/0378722 | A1 | 12/2022 | Demario et al. |

(Continued)

FOREIGN PATENT DOCUMENTS

| | | |
|---|---|---|
| CA | 3071804 | 2/2019 |
| EA | 26389 | 4/2017 |
| RU | 2611437 | 2/2017 |

(Continued)

OTHER PUBLICATIONS

Lanius (Neuropsychologia 90 (2016) 210-234), (Year: 2016).*
Oryzon Genomics: "Oryzon receives approval to begin Reimagine: a Phase IIa clinical trial with Vafidemstat (ORY-2001) in aggressiveness", Madrid Stock Exchange: ORY.MC, Sep. 7, 2018, (XP055697778), https://www.globenewswire.com/news-release/2018/09/07/1567968/0/en/Oryzon-receives-approval-to-begin-REIMAGINE-a-Phase-IIa-clinical-trial-with-Vafidemstat-in-aggressiveness.html.

(Continued)

*Primary Examiner* — John S Kenyon
*Assistant Examiner* — Rehana Ismail
(74) *Attorney, Agent, or Firm* — FINNEGAN, HENDERSON, FARABOW, GARRETT & DUNNER, LLP

(57) ABSTRACT

Provided herein are methods for treating borderline personality disorder using KDMIA inhibitors, particularly vafidemstat.

11 Claims, 3 Drawing Sheets

(56) References Cited

U.S. PATENT DOCUMENTS

| | | | |
|---|---|---|---|
| 2024/0226069 | A1 | 7/2024 | Buesa Arjol et al. |
| 2024/0277673 | A1 | 8/2024 | Maes et al. |

FOREIGN PATENT DOCUMENTS

| | | | |
|---|---|---|---|
| RU | 2668952 | 10/2018 | |
| WO | WO2010/043721 | 4/2010 | |
| WO | WO2010/084160 | 7/2010 | |
| WO | WO2011/035941 | 3/2011 | |
| WO | WO2011/042217 | 4/2011 | |
| WO | WO2011/106105 | 9/2011 | |
| WO | WO2011/106106 | 9/2011 | |
| WO | WO2011/131697 | 10/2011 | |
| WO | WO2012/013727 | 2/2012 | |
| WO | WO2012/013728 | 2/2012 | |
| WO | WO2012/042042 | 4/2012 | |
| WO | WO2012/045883 | 4/2012 | |
| WO | WO2012/072713 | 6/2012 | |
| WO | WO2012/107498 | 8/2012 | |
| WO | WO2012/107499 | 8/2012 | |
| WO | WO2012/156531 | 11/2012 | |
| WO | WO2012/156537 | 11/2012 | |
| WO | WO2013/025805 | 2/2013 | |
| WO | WO2013/057320 | 4/2013 | |
| WO | WO2013/057322 | 4/2013 | |
| WO | WO2016/177656 | 11/2016 | |
| WO | WO2016/198649 | 12/2016 | |
| WO | WO2017/013061 | 1/2017 | |
| WO | WO2017/060319 | 4/2017 | |
| WO | WO2017/157813 | 9/2017 | |
| WO | WO2017/157825 | 9/2017 | |
| WO | WO2017/158136 | 9/2017 | |
| WO | WO2017/212061 | 12/2017 | |
| WO | WO2018/083138 | 5/2018 | |
| WO | WO2018/083189 | 5/2018 | |
| WO | WO2019/025588 | 2/2019 | |
| WO | WO-2019025588 A1 * | 2/2019 | .............. A61P 25/16 |
| WO | WO2019/211491 | 11/2019 | |
| WO | WO2020/188089 | 9/2020 | |
| WO | WO2020/188090 | 9/2020 | |
| WO | WO2020/193631 | 10/2020 | |
| WO | WO2021004610 | 1/2021 | |
| WO | WO2021043905 | 3/2021 | |

OTHER PUBLICATIONS

Oryzon Genomics: Press release 2019 "Oryzon to present first in human efficacy data with Vafidemstat at the 27th European Congress of Psychiatry in Warsaw", Apr. 8, 2019 (XP055697784), https://www.oryzon.com/sites/default/files/PRESS_RELEASE_10-2019.pdf.

Ripoll, "Psychopharmacologic treatment of borderline personality disorder", Dialogues Clin Neurosci, 2013, 15(2):213-224.

Yang et al., "Pharmacological Inhibition of LSD1 for Cancer Treatment", Molecules, 2018, 23(12):3194, pp. 1-20.

Mimasu et al., "Structurally designed trans-2-phenylcyclopropylamine derivatives potently inhibit histone demethylase LSD1/KDM1", Biochemistry, 2010, 49(30):6494-6503.

International Search Report of International Application No. PCT/EP2020/057803.

Written Opinion of the International Searching Authority of International Application No. PCT/EP2020/057803.

Co-pending U.S. Appl. No. 18/813,129, filed Aug. 23, 2024.

Co-pending U.S. Appl. No. 18/437,304, filed Feb. 9, 2024.

Co-pending U.S. Appl. No. 17/644,604, filed Dec. 16, 2021.

Co-pending U.S. Appl. No. 18/912,810, filed Oct. 11, 2024.

Co-pending U.S. Appl. No. 18/670,941, filed May 22, 2024.

Co-pending U.S. Appl. No. 18/748,442, filed Jun. 20, 2024.

Bullock et al., "P97: Using transcription phenotypes to utilise basket trial methodology from oncology to create new targets in CNS disorders", The Journal of Prevention of Alzheimer's Disease, 2018, vol. 5, Supplement 1, S54-S55.

CAS registry entry for 1357362-02-7, entered on Feb. 23, 2012.

McKinnon et al., "A review of the relation between dissociation, memory, executive functioning and social cognition in military members and civilians with neuropsychiatric conditions", Neuropsychologia, 2016, 90, 210-234.

* cited by examiner

METHODS OF TREATING BORDERLINE PERSONALITY DISORDER

This application is a national stage filing under 35 U.S.C. § 371 of International Application No. PCT/EP2020/057803, filed on Mar. 20, 2020, which claims benefit of European Patent Application Nos. 19382196.4, filed on Mar. 20, 2019, all of which are incorporated herein by reference.

FIELD

The present invention relates to methods for treating borderline personality disorder.

BACKGROUND

Borderline personality disorder (BPD) is one of the most complex, functionally debilitating and costly psychiatric conditions currently facing the mental health systems. The essential features of BPD are impairments in personality (self and interpersonal) functioning and the presence of pathological personality traits. Patients with BPD typically experience emotional instability, impulsivity, irrational beliefs and distorted perception, as well as intense but unstable relationships with others. Up to 10% of people affected die by suicide. Women are diagnosed about three times as often as men.

The treatment of BPD remains a medical challenge. There are currently no approved drugs by the FDA to specifically treat BPD. Medications such as mood stabilizers and atypical antipsychotics are used off-label to treat BPD, but with questionable efficacy and unwanted side effects such as sedation and weight gain.

Thus, there is a strong and unmet medical need for new and/or improved drugs for treating BPD, particularly drugs that act via novel mechanisms of action and treat the core features of BPD, and with a more favorable side effect profile than current non-specific off-label therapies. The present invention addresses these and other needs.

SUMMARY OF THE INVENTION

The invention provides novel methods for treating borderline personality disorder by using KDM1A inhibitors. Thus, the present invention provides a KDM1A inhibitor for use in the treatment of borderline personality disorder.

The present invention further provides a method for treating borderline personality disorder in a patient (preferably a human), comprising administering to the patient a therapeutically effective amount of a KDM1A inhibitor.

The present invention further provides the use of a KDM1A inhibitor for the manufacture of a medicament for the treatment of borderline personality disorder.

The present invention further provides the use of a KDM1A inhibitor for the treatment of borderline personality disorder.

In preferred embodiments, the KDM1A inhibitor is vafidemstat or a pharmaceutically acceptable salt or solvate thereof.

DETAILED DESCRIPTION OF THE INVENTION

Figure 1:
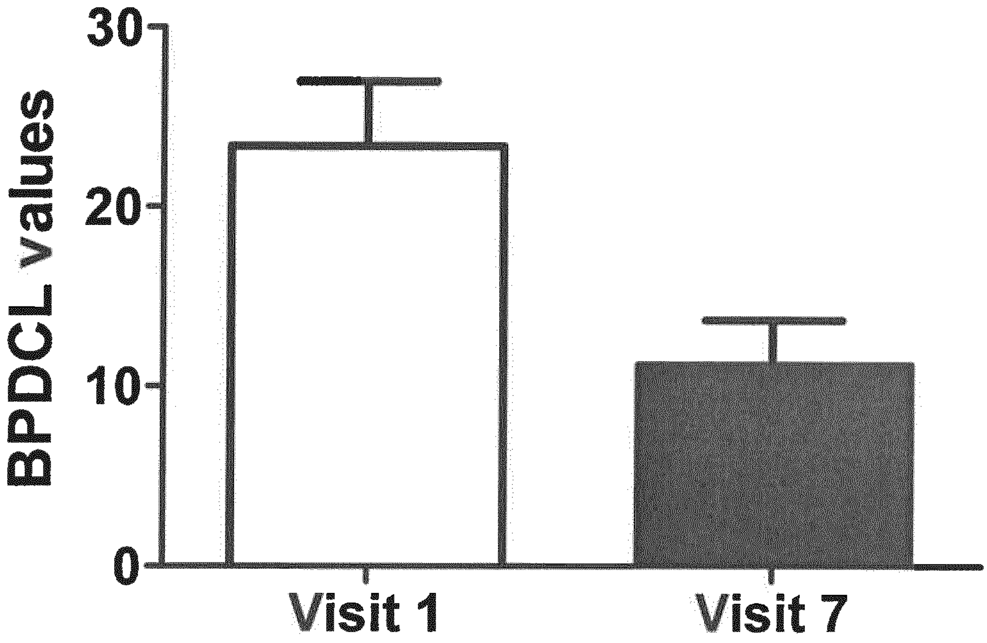
FIG. 1 shows the effect of treatment with the KDM1A inhibitor vafidemstat (as defined herein and in Example 1) to treat aggression in human BPD patients, as shown by a statistically significant reduction in the Aggression-related BPDCL domains combined score from visit 1 (baseline, pre-treatment) to visit 7 (8 weeks treatment with vafidemstat), as described in more detail in Example 3. Data is represented as mean±standard error of the mean (SEM); p=0.0029.

The invention is based on the unexpected finding that KDM1A inhibitors are useful as therapeutic agents to treat BPD. KDM1A inhibitors, including vafidemstat, have been reported to be useful to reduce aggressiveness, such as aggressiveness associated with a disease, without sedative effects. Vafidemstat is currently in a Phase IIa clinical trial treating aggression in patients with Alzheimer's disease, Lewy Body dementia, autistic spectrum disorder, attention deficit hyperactivity disorder and BPD (REIMAGINE trial). Results of this clinical trial unexpectedly demonstrated that vafidemstat is not only effective to treat aggression in BPD patients, but exhibits additional therapeutic effects on BPD, as detailed below and in the Examples. KDM1A inhibitors and particularly vafidemstat are useful as a treatment for BPD, including treating (non-aggressive) core features of BPD, as defined below.

Accordingly, the present invention provides a KDM1A inhibitor for use in the treatment of BPD.

The present invention further provides a method for treating BPD in a patient (preferably a human), comprising administering to the patient a therapeutically effective amount of a KDM1A inhibitor.

The present invention further provides the use of a KDM1A inhibitor for the manufacture of a medicament for the treatment of BPD.

The present invention further provides the use of a KDM1A inhibitor for the treatment of BPD.

In some embodiments, the present invention provides a KDM1A inhibitor for use in the treatment of BPD by treating one or more core features of BPD.

In some embodiments, the present invention provides a method for treating BPD in a patient (preferably a human) by treating (e.g. alleviating or improving) one or more core features of BPD, the method comprising administering to the patient a therapeutically effective amount of a KDM1A inhibitor.

In some embodiments, the present invention provides the use of a KDM1A inhibitor for the manufacture of a medicament for the treatment of BPD by treating (e.g. alleviating or improving) one or more core features of BPD.

In some embodiments, the present invention provides the use of a KDM1A inhibitor for the treatment of BPD by treating (e.g. alleviating or improving) one or more core features of BPD.

In accordance with the present invention, "core feature(s) of BPD" mean the essential features of BPD according to the Diagnostic and Statistical Manual of Mental Disorders, Fifth Edition (DSM-5), as published by the American Psychiatric Association, and which include impairments in personality (self and interpersonal) functioning and the presence of pathological personality traits.

In some embodiments, the present invention provides a KDM1A inhibitor for use in the treatment of BPD by treating (e.g. alleviating or improving) one or more non-aggressive symptoms of BPD.

In some embodiments, the present invention provides a method for treating BPD in a patient (preferably a human) by treating (e.g. alleviating or improving) one or more non-aggressive symptoms of BPD, the method comprising administering to the patient a therapeutically effective amount of a KDM1A inhibitor.

In some embodiments, the present invention provides the use of a KDM1A inhibitor for the manufacture of a medicament for the treatment of BPD by treating (e.g. alleviating or improving) one or more non-aggressive symptoms of BPD.

In some embodiments, the present invention provides the use of a KDM1A inhibitor for the treatment of BPD by treating (e.g. alleviating or improving) one or more non-aggressive symptoms of BPD.

In accordance with the present invention, "non-aggressive" as for example used in the context of a BPD symptom means that said symptom of BPD is not directly related to or associated with aggression or aggressive behavior. "Aggression", "aggressive" and related terms, as used herein, refer to any kind of abnormal, pathological or inappropriate aggressive or violent behavior, hostility or agitation, for example physical or verbal, including interpersonal aggressiveness (i.e. towards other subjects) and/or intrapersonal aggressiveness (i.e. self-aggressiveness).

Examples of non-aggressive symptoms of BPD include emotional instability, irrational beliefs, intense but unstable relationships with others, abandonment, identity disturbance, emptiness, and dissociation.

In some embodiments, the present invention provides a KDM1A inhibitor for use in the treatment of BPD by treating (e.g. alleviating or improving) one or more core features of BPD and by treating (e.g. reducing) aggression.

In some embodiments, the present invention provides a method for treating BPD in a patient (preferably a human) by treating (e.g. alleviating or improving) one or more core features of BPD and by treating (e.g. reducing) aggression, the method comprising administering to the patient a therapeutically effective amount of a KDM1A inhibitor.

In some embodiments, the present invention provides the use of a KDM1A inhibitor for the manufacture of a medicament for the treatment of BPD by treating (e.g. alleviating or improving) one or more core features of BPD and by treating (e.g. reducing) aggression.

In some embodiments, the present invention provides the use of a KDM1A inhibitor for the treatment of BPD by treating (e.g. alleviating or improving) one or more core features of BPD and by treating (e.g. reducing) aggression.

In some embodiments, the present invention provides a KDM1A inhibitor for use in the treatment of BPD by treating (e.g. alleviating or improving) one or more non-aggressive symptoms of BPD and by treating (e.g. reducing) aggression.

In some embodiments, the present invention provides a method for treating BPD in a patient (preferably a human) by treating (e.g. alleviating or improving) one or more non-aggressive symptoms of BPD and by treating (e.g. reducing) aggression, the method comprising administering to the patient a therapeutically effective amount of a KDM1A inhibitor.

In some embodiments, the present invention provides the use of a KDM1A inhibitor for the manufacture of a medicament for the treatment of BPD by treating (e.g. alleviating or improving) one or more non-aggressive symptoms of BPD and by treating (e.g. reducing) aggression.

In some embodiments, the present invention provides the use of a KDM1A inhibitor for the treatment of BPD by treating (e.g. alleviating or improving) one or more non-aggressive symptoms of BPD and by treating (e.g. reducing) aggression.

In some embodiments, the present invention provides a KDM1A inhibitor for use in the treatment of BPD by treating (e.g. alleviating or improving) one or more core features of BPD and by treating (e.g. reducing) agitation.

In some embodiments, the present invention provides a method for treating BPD in a patient (preferably a human) by treating (e.g. alleviating or improving) one or more core features of BPD and by treating (e.g. reducing) agitation, the method comprising administering to the patient a therapeutically effective amount of a KDM1A inhibitor.

In some embodiments, the present invention provides the use of a KDM1A inhibitor for the manufacture of a medicament for the treatment of BPD by treating (e.g. alleviating or improving) one or more core features of BPD and by treating (e.g. reducing) agitation.

In some embodiments, the present invention provides the use of a KDM1A inhibitor for the treatment of BPD by treating (e.g. alleviating or improving) one or more core features of BPD and by treating (e.g. reducing) agitation.

In some embodiments, the present invention provides a KDM1A inhibitor for use in the treatment of BPD by treating (e.g. alleviating or improving) one or more non-aggressive symptoms of BPD and by treating (e.g. reducing) agitation.

In some embodiments, the present invention provides a method for treating BPD in a patient (preferably a human) by treating (e.g. alleviating or improving) one or more non-aggressive symptoms of BPD and by treating (e.g. reducing) agitation, the method comprising administering to the patient a therapeutically effective amount of a KDM1A inhibitor.

In some embodiments, the present invention provides the use of a KDM1A inhibitor for the manufacture of a medicament for the treatment of BPD by treating (e.g. alleviating or improving) one or more non-aggressive symptoms of BPD and by treating (e.g. reducing) agitation.

In some embodiments, the present invention provides the use of a KDM1A inhibitor for the treatment of BPD by treating (e.g. alleviating or improving) one or more non-aggressive symptoms of BPD and by treating (e.g. reducing) agitation.

In some embodiments, the present invention provides a KDM1A inhibitor for use in the treatment of BPD by treating (e.g. alleviating or improving) one or more core features of BPD and by treating (e.g. reducing) agitation and aggression.

In some embodiments, the present invention provides a method for treating BPD in a patient (preferably a human) by treating (e.g. alleviating or improving) one or more core features of BPD and by treating (e.g. reducing) agitation and aggression, the method comprising administering to the patient a therapeutically effective amount of a KDM1A inhibitor.

In some embodiments, the present invention provides the use of a KDM1A inhibitor for the manufacture of a medicament for the treatment of BPD by treating (e.g. alleviating or improving) one or more core features of BPD and by treating (e.g. reducing) agitation and aggression.

In some embodiments, the present invention provides the use of a KDM1A inhibitor for the treatment of BPD by treating (e.g. alleviating or improving) one or more core features of BPD and by treating (e.g. reducing) agitation and aggression.

In some embodiments, the present invention provides a KDM1A inhibitor for use in the treatment of BPD by treating (e.g. alleviating or improving) one or more non-aggressive symptoms of BPD and by treating (e.g. reducing) agitation and aggression.

In some embodiments, the present invention provides a method for treating BPD in a patient (preferably a human) by treating (e.g. alleviating or improving) one or more non-aggressive symptoms of BPD and by treating (e.g. reducing) agitation and aggression, the method comprising administering to the patient a therapeutically effective amount of a KDM1A inhibitor.

In some embodiments, the present invention provides the use of a KDM1A inhibitor for the manufacture of a medicament for the treatment of BPD by treating (e.g. alleviating or improving) one or more non-aggressive symptoms of BPD and by treating (e.g. reducing) agitation and aggression.

In some embodiments, the present invention provides the use of a KDM1A inhibitor for the treatment of BPD by treating (e.g. alleviating or improving) one or more non-aggressive symptoms of BPD and by treating (e.g. reducing) agitation and aggression.

In some embodiments, the present invention provides a KDM1A inhibitor for use in the treatment of a BPD patient by treating (e.g. alleviating or improving) one or more core features of BPD.

In some embodiments, the present invention provides a method for treating a BPD patient (preferably a human) by treating (e.g. alleviating or improving) one or more core features of BPD, the method comprising administering to the patient a therapeutically effective amount of a KDM1A inhibitor.

In some embodiments, the present invention provides the use of a KDM1A inhibitor for the manufacture of a medicament for the treatment of a BPD patient by treating (e.g. alleviating or improving) one or more core features of BPD.

In some embodiments, the present invention provides the use of a KDM1A inhibitor for the treatment of a BPD patient by treating (e.g. alleviating or improving) one or more core features of BPD.

In some embodiments, the present invention provides a KDM1A inhibitor for use in the treatment of a BPD patient by treating (e.g. alleviating or improving) one or more non-aggressive symptoms of BPD.

In some embodiments, the present invention provides a method for treating a BPD patient (preferably a human) by treating (e.g. alleviating or improving) one or more non-aggressive symptoms of BPD, the method comprising administering to the patient a therapeutically effective amount of a KDM1A inhibitor.

In some embodiments, the present invention provides the use of a KDM1A inhibitor for the manufacture of a medicament for the treatment of a BPD patient by treating (e.g. alleviating or improving) one or more non-aggressive symptoms of BPD.

In some embodiments, the present invention provides the use of a KDM1A inhibitor for the treatment of a BPD patient by treating (e.g. alleviating or improving) one or more non-aggressive symptoms of BPD.

In some embodiments, the present invention provides a KDM1A inhibitor for use in the treatment of a BPD patient by treating (e.g. alleviating or improving) one or more core features of BPD and by treating (e.g. reducing) aggression.

In some embodiments, the present invention provides a method for treating a BPD patient (preferably a human) by treating (e.g. alleviating or improving) one or more core features of BPD and by treating (e.g. reducing) aggression, the method comprising administering to the patient a therapeutically effective amount of a KDM1A inhibitor.

In some embodiments, the present invention provides the use of a KDM1A inhibitor for the manufacture of a medicament for the treatment of a BPD patient by treating (e.g. alleviating or improving) one or more core features of BPD and by treating (e.g. reducing) aggression.

In some embodiments, the present invention provides the use of a KDM1A inhibitor for the treatment of a BPD patient by treating (e.g. alleviating or improving) one or more core features of BPD and by treating (e.g. reducing) aggression.

In some embodiments, the present invention provides a KDM1A inhibitor for use in the treatment of a BPD patient by treating (e.g. alleviating or improving) one or more non-aggressive symptoms of BPD and by treating (e.g. reducing) aggression.

In some embodiments, the present invention provides a method for treating a BPD patient (preferably a human) by treating (e.g. alleviating or improving) one or more non-aggressive symptoms of BPD and by treating (e.g. reducing) aggression, the method comprising administering to the patient a therapeutically effective amount of a KDM1A inhibitor.

In some embodiments, the present invention provides the use of a KDM1A inhibitor for the manufacture of a medicament for the treatment of a BPD patient by treating (e.g. alleviating or improving) one or more non-aggressive symptoms of BPD and by treating (e.g. reducing) aggression.

In some embodiments, the present invention provides the use of a KDM1A inhibitor for the treatment of a BPD patient by treating (e.g. alleviating or improving) one or more non-aggressive symptoms of BPD and by treating (e.g. reducing) aggression.

In some embodiments, the present invention provides a KDM1A inhibitor for use in the treatment of a BPD patient by treating (e.g. alleviating or improving) one or more core features of BPD and by treating (e.g. reducing) agitation.

In some embodiments, the present invention provides a method for treating a BPD patient (preferably a human) by treating (e.g. alleviating or improving) one or more core features of BPD and by treating (e.g. reducing) agitation, the method comprising administering to the patient a therapeutically effective amount of a KDM1A inhibitor.

In some embodiments, the present invention provides the use of a KDM1A inhibitor for the manufacture of a medicament for the treatment of a BPD patient by treating (e.g. alleviating or improving) one or more core features of BPD and by treating (e.g. reducing) agitation.

In some embodiments, the present invention provides the use of a KDM1A inhibitor for the treatment of a BPD patient by treating (e.g. alleviating or improving) one or more core features of BPD and by treating (e.g. reducing) agitation.

In some embodiments, the present invention provides a KDM1A inhibitor for use in the treatment of a BPD patient by treating (e.g. alleviating or improving) one or more non-aggressive symptoms of BPD and by treating (e.g. reducing) agitation.

In some embodiments, the present invention provides a method for treating a BPD patient (preferably a human) by treating (e.g. alleviating or improving) one or more non-aggressive symptoms of BPD and by treating (e.g. reducing) agitation, the method comprising administering to the patient a therapeutically effective amount of a KDM1A inhibitor.

In some embodiments, the present invention provides the use of a KDM1A inhibitor for the manufacture of a medicament for the treatment of a BPD patient by treating (e.g. alleviating or improving) one or more non-aggressive symptoms of BPD and by treating (e.g. reducing) agitation.

In some embodiments, the present invention provides the use of a KDM1A inhibitor for the treatment of a BPD patient by treating (e.g. alleviating or improving) one or more non-aggressive symptoms of BPD and by treating (e.g. reducing) agitation.

In some embodiments, the present invention provides a KDM1A inhibitor for use in the treatment of a BPD patient by treating (e.g. alleviating or improving) one or more core features of BPD and by treating (e.g. reducing) agitation and aggression.

In some embodiments, the present invention provides a method for treating a BPD patient (preferably a human) by treating (e.g. alleviating or improving) one or more core features of BPD and by treating (e.g. reducing) agitation and aggression, the method comprising administering to the patient a therapeutically effective amount of a KDM1A inhibitor.

In some embodiments, the present invention provides the use of a KDM1A inhibitor for the manufacture of a medicament for the treatment of a BPD patient by treating (e.g. alleviating or improving) one or more core features of BPD and by treating (e.g. reducing) agitation and aggression.

In some embodiments, the present invention provides the use of a KDM1A inhibitor for the treatment of a BPD patient by treating (e.g. alleviating or improving) one or more core features of BPD and by treating (e.g. reducing) agitation and aggression.

In some embodiments, the present invention provides a KDM1A inhibitor for use in the treatment of a BPD patient by treating (e.g. alleviating or improving) one or more non-aggressive symptoms of BPD and by treating (e.g. reducing) agitation and aggression.

In some embodiments, the present invention provides a method for treating a BPD patient (preferably a human) by treating (e.g. alleviating or improving) one or more non-aggressive symptoms of BPD and by treating (e.g. reducing) agitation and aggression, the method comprising administering to the patient a therapeutically effective amount of a KDM1A inhibitor.

In some embodiments, the present invention provides the use of a KDM1A inhibitor for the manufacture of a medicament for the treatment of a BPD patient by treating (e.g. alleviating or improving) one or more non-aggressive symptoms of BPD and by treating (e.g. reducing) agitation and aggression.

In some embodiments, the present invention provides the use of a KDM1A inhibitor for the treatment of a BPD patient by treating (e.g. alleviating or improving) one or more non-aggressive symptoms of BPD and by treating (e.g. reducing) agitation and aggression.

In some embodiments, the present invention provides a KDM1A inhibitor for use in the treatment of one or more core features of BPD.

In some embodiments, the present invention provides a method for treating one or more core features of BPD in a patient (preferably a human), the method comprising administering to the patient a therapeutically effective amount of a KDM1A inhibitor.

In some embodiments, the present invention provides the use of a KDM1A inhibitor for the manufacture of a medicament for the treatment of one or more core features of BPD.

In some embodiments, the present invention provides the use of a KDM1A inhibitor for the treatment of one or more core features of BPD.

In some embodiments, the present invention provides a KDM1A inhibitor for use in the treatment of one or more non-aggressive symptoms of BPD.

In some embodiments, the present invention provides a method for treating one or more non-aggressive symptoms of BPD in a patient (preferably a human), comprising administering to the patient a therapeutically effective amount of a KDM1A inhibitor.

In some embodiments, the present invention provides the use of a KDM1A inhibitor for the manufacture of a medicament for the treatment of one or more non-aggressive symptoms of BPD.

In some embodiments, the present invention provides the use of a KDM1A inhibitor for the treatment of one or more non-aggressive symptoms of BPD.

In some embodiments, the present invention provides a KDM1A inhibitor for use in the treatment of one or more core features of BPD as well as agitation and/or aggression.

In some embodiments, the present invention provides a method for treating one or more core features of BPD as well as agitation and/or aggression in a patient (preferably a human), the method comprising administering to the patient a therapeutically effective amount of a KDM1A inhibitor.

In some embodiments, the present invention provides the use of a KDM1A inhibitor for the manufacture of a medicament for the treatment of one or more core features of BPD as well as agitation and/or aggression.

In some embodiments, the present invention provides the use of a KDM1A inhibitor for the treatment of one or more core features of BPD as well as agitation and/or aggression.

In some embodiments, the present invention provides a KDM1A inhibitor for use in the treatment of one or more non-aggressive symptoms of BPD as well as agitation and/or aggression.

In some embodiments, the present invention provides a method for treating one or more non-aggressive symptoms of BPD as well as agitation and/or aggression in a patient (preferably a human), the method comprising administering to the patient a therapeutically effective amount of a KDM1A inhibitor.

In some embodiments, the present invention provides the use of a KDM1A inhibitor for the manufacture of a medicament for the treatment of one or more non-aggressive symptoms of BPD as well as agitation and/or aggression.

In some embodiments, the present invention provides the use of a KDM1A inhibitor for the treatment of one or more non-aggressive symptoms of BPD as well as agitation and/or aggression.

Also provided herein is a KDM1A inhibitor for use in the treatment (e.g. reduction) of agitation in BPD. Likewise provided herein is a KDM1A inhibitor for use in the treatment (e.g. reduction) of agitation in a BPD patient. Further provided herein is a KDM1A inhibitor for use in the treatment of a BPD patient by treating (e.g. reducing) agitation. Provided herein is furthermore a method for treating (e.g., reducing) agitation in a BPD patient (preferably a human), comprising administering to the patient a therapeutically effective amount of a KDM1A inhibitor. Likewise provided herein is the use of a KDM1A inhibitor for the manufacture of a medicament for the treatment (e.g. reduction) of agitation in BPD. Further provided herein is the use of a KDM1A inhibitor for the treatment (e.g. reduction) of agitation in BPD.

Moreover, provided herein is also a KDM1A inhibitor for use in the treatment (e.g. reduction) of aggression in BPD. Likewise provided herein is a KDM1A inhibitor for use in the treatment (e.g. reduction) of aggression in a BPD patient. Further provided herein is a KDM1A inhibitor for use in the treatment of a BPD patient by treating (e.g. reducing) aggression. Further provided herein is a method for treating (e.g., reducing) aggression in a BPD patient (preferably a human), comprising administering to the patient a therapeutically effective amount of a KDM1A inhibitor. Likewise provided herein is the use of a KDM1A inhibitor for the manufacture of a medicament for the treatment (e.g. reduction) of aggression in BPD. Provided herein is furthermore the use of a KDM1A inhibitor for the treatment (e.g. reduction) of aggression in BPD.

In the methods of treatment and therapeutic uses as described herein any KDM1A inhibitor may in principle be used, including the KDM1A inhibitors as described in more detail herein below. It is however preferred that the KDM1A inhibitor for use in the methods and uses of the invention is the compound 5-((((1R,2S)-2-(4-(benzyloxy)phenyl)cyclopropyl)amino)methyl)-1,3,4-oxadiazol-2-amine, also known as (41R,42S)-6-oxa-3-aza-1(2)-[1,3,4]oxadiazola-5(1,4),8(1)-dibenzena-4(1,2)-cyclopropanaoctaphan-15-amine, vafidemstat (INN) or ORY-2001, or a pharmaceutically acceptable salt or solvate thereof, and it is particularly preferred that the KDM1A inhibitor is the compound 5-((((1R,2S)-2-(4-(benzyloxy)phenyl)cyclopropyl)amino)methyl)-1,3,4-oxadiazol-2-amine (in non-salt form). The names "5-((((1R,2S)-2-(4-(benzyloxy)phenyl)cyclopropyl)amino)methyl)-1,3,4-oxadiazol-2-amine", "(41R,42S)-6-oxa-3-aza-1(2)-[1,3,4]oxadiazola-5(1,4),8(1)-dibenzena-4(1,2)-cyclopropanaoctaphan-15-amine", "vafidemstat" or "ORY-2001" are used herein interchangeably.

Accordingly, the present invention provides vafidemstat, or a pharmaceutically acceptable salt or solvate thereof, for use in the treatment of BPD.

The present invention further provides a method for treating BPD in a patient (preferably a human), comprising administering to the patient a therapeutically effective amount of vafidemstat, or a pharmaceutically acceptable salt or solvate thereof.

The present invention further provides the use of vafidemstat, or a pharmaceutically acceptable salt or solvate thereof, for the manufacture of a medicament for the treatment of BPD.

The present invention further provides the use of vafidemstat, or a pharmaceutically acceptable salt or solvate thereof, for the treatment of BPD.

In some embodiments, the present invention provides vafidemstat, or a pharmaceutically acceptable salt or solvate thereof, for use in the treatment of BPD by treating (e.g. alleviating or improving) one or more core features of BPD.

In some embodiments, the present invention provides a method for treating BPD in a patient (preferably a human) by treating (e.g. alleviating or improving) one or more core features of BPD, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of BPD by treating (e.g. alleviating or improving) one or more core features of BPD.

In some embodiments, the present invention provides the use of vafidemstat, or a pharmaceutically acceptable salt or solvate thereof, for the treatment of BPD by treating (e.g. alleviating or improving) one or more core features of BPD.

In some embodiments, the present invention provides vafidemstat, or a pharmaceutically acceptable salt or solvate thereof, for use in the treatment of BPD by treating (e.g. alleviating or improving) one or more non-aggressive symptoms of BPD.

In some embodiments, the present invention provides a method for treating BPD in a patient (preferably a human) by treating (e.g. alleviating or improving) one or more non-aggressive symptoms of BPD, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of BPD by treating (e.g. alleviating or improving) one or more non-aggressive symptoms of BPD.

In some embodiments, the present invention provides the use of vafidemstat, or a pharmaceutically acceptable salt or solvate thereof, for the treatment of BPD by treating (e.g. alleviating or improving) one or more non-aggressive symptoms of BPD.

In some embodiments, the present invention provides vafidemstat, or a pharmaceutically acceptable salt or solvate thereof, for use in the treatment of BPD by treating (e.g. alleviating or improving) one or more core features of BPD and by treating (e.g. reducing) aggression.

In some embodiments, the present invention provides a method for treating BPD in a patient (preferably a human) by treating (e.g. alleviating or improving) one or more core features of BPD and by treating (e.g. reducing) aggression, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of BPD by treating (e.g. alleviating or improving) one or more core features of BPD and by treating (e.g. reducing) aggression.

In some embodiments, the present invention provides the use of vafidemstat, or a pharmaceutically acceptable salt or solvate thereof, for the treatment of BPD by treating (e.g. alleviating or improving) one or more core features of BPD and by treating (e.g. reducing) aggression.

In some embodiments, the present invention provides vafidemstat, or a pharmaceutically acceptable salt or solvate thereof, for use in the treatment of BPD by treating (e.g. alleviating or improving) one or more non-aggressive symptoms of BPD and by treating (e.g. reducing) aggression.

In some embodiments, the present invention provides a method for treating BPD in a patient (preferably a human) by treating (e.g. alleviating or improving) one or more non-aggressive symptoms of BPD and by treating (e.g. reducing) aggression, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of BPD by treating (e.g. alleviating or improving) one or more non-aggressive symptoms of BPD and by treating (e.g. reducing) aggression.

In some embodiments, the present invention provides the use of vafidemstat, or a pharmaceutically acceptable salt or solvate thereof, for the treatment of BPD by treating (e.g. alleviating or improving) one or more non-aggressive symptoms of BPD and by treating (e.g. reducing) aggression.

In some embodiments, the present invention provides vafidemstat, or a pharmaceutically acceptable salt or solvate thereof, for use in the treatment of BPD by treating (e.g. alleviating or improving) one or more core features of BPD and by treating (e.g. reducing) agitation.

In some embodiments, the present invention provides a method for treating BPD in a patient (preferably a human) by treating (e.g. alleviating or improving) one or more core features of BPD and by treating (e.g. reducing) agitation, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of BPD by treating (e.g. alleviating or improving) one or more core features of BPD and by treating (e.g. reducing) agitation.

In some embodiments, the present invention provides the use of vafidemstat, or a pharmaceutically acceptable salt or solvate thereof, for the treatment of BPD by treating (e.g. alleviating or improving) one or more core features of BPD and by treating (e.g. reducing) agitation.

In some embodiments, the present invention provides vafidemstat, or a pharmaceutically acceptable salt or solvate thereof, for use in the treatment of BPD by treating (e.g. alleviating or improving) one or more non-aggressive symptoms of BPD and by treating (e.g. reducing) agitation.

In some embodiments, the present invention provides a method for treating BPD in a patient (preferably a human) by treating (e.g. alleviating or improving) one or more non-aggressive symptoms of BPD and by treating (e.g. reducing) agitation, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of BPD by treating (e.g. alleviating or improving) one or more non-aggressive symptoms of BPD and by treating (e.g. reducing) agitation.

In some embodiments, the present invention provides the use of vafidemstat, or a pharmaceutically acceptable salt or solvate thereof, for the treatment of BPD by treating (e.g. alleviating or improving) one or more non-aggressive symptoms of BPD and by treating (e.g. reducing) agitation.

In some embodiments, the present invention provides vafidemstat, or a pharmaceutically acceptable salt or solvate thereof, for use in the treatment of BPD by treating (e.g. alleviating or improving) one or more core features of BPD and by treating (e.g. reducing) agitation and aggression.

In some embodiments, the present invention provides a method for treating BPD in a patient (preferably a human) by treating (e.g. alleviating or improving) one or more core features of BPD and by treating (e.g. reducing) agitation and aggression, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of BPD by treating (e.g. alleviating or improving) one or more core features of BPD and by treating (e.g. reducing) agitation and aggression.

In some embodiments, the present invention provides the use of vafidemstat, or a pharmaceutically acceptable salt or solvate thereof, for the treatment of BPD by treating (e.g. alleviating or improving) one or more core features of BPD and by treating (e.g. reducing) agitation and aggression.

In some embodiments, the present invention provides vafidemstat, or a pharmaceutically acceptable salt or solvate thereof, for use in the treatment of BPD by treating (e.g. alleviating or improving) one or more non-aggressive symptoms of BPD and by treating (e.g. reducing) agitation and aggression.

In some embodiments, the present invention provides a method for treating BPD in a patient (preferably a human) by treating (e.g. alleviating or improving) one or more non-aggressive symptoms of BPD and by treating (e.g. reducing) agitation and aggression, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of BPD by treating (e.g. alleviating or improving) one or more non-aggressive symptoms of BPD and by treating (e.g. reducing) agitation and aggression.

In some embodiments, the present invention provides the use of vafidemstat, or a pharmaceutically acceptable salt or solvate thereof, for the treatment of BPD by treating (e.g. alleviating or improving) one or more non-aggressive symptoms of BPD and by treating (e.g. reducing) agitation and aggression.

In some embodiments, the present invention provides vafidemstat, or a pharmaceutically acceptable salt or solvate thereof, for use in the treatment of a BPD patient by treating (e.g. alleviating or improving) one or more core features of BPD.

In some embodiments, the present invention provides a method for treating a BPD patient (preferably a human) by treating (e.g. alleviating or improving) one or more core features of BPD, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of a BPD patient by treating (e.g. alleviating or improving) one or more core features of BPD.

In some embodiments, the present invention provides the use of vafidemstat, or a pharmaceutically acceptable salt or solvate thereof, for the treatment of a BPD patient by treating (e.g. alleviating or improving) one or more core features of BPD.

In some embodiments, the present invention provides vafidemstat, or a pharmaceutically acceptable salt or solvate thereof, for use in the treatment of a BPD patient by treating (e.g. alleviating or improving) one or more non-aggressive symptoms of BPD.

In some embodiments, the present invention provides a method for treating a BPD patient (preferably a human) by treating (e.g. alleviating or improving) one or more non-aggressive symptoms of BPD, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of a BPD patient by treating (e.g. alleviating or improving) one or more non-aggressive symptoms of BPD.

In some embodiments, the present invention provides the use of vafidemstat, or a pharmaceutically acceptable salt or solvate thereof, for the treatment of a BPD patient by treating (e.g. alleviating or improving) one or more non-aggressive symptoms of BPD.

In some embodiments, the present invention provides vafidemstat, or a pharmaceutically acceptable salt or solvate thereof, for use in the treatment of a BPD patient by treating (e.g. alleviating or improving) one or more core features of BPD and by treating (e.g. reducing) aggression.

In some embodiments, the present invention provides a method for treating a BPD patient (preferably a human) by treating (e.g. alleviating or improving) one or more core features of BPD and by treating (e.g. reducing) aggression, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of a BPD patient by treating (e.g. alleviating or improving) one or more core features of BPD and by treating (e.g. reducing) aggression.

In some embodiments, the present invention provides the use of vafidemstat, or a pharmaceutically acceptable salt or solvate thereof, for the treatment of a BPD patient by treating (e.g. alleviating or improving) one or more core features of BPD and by treating (e.g. reducing) aggression.

In some embodiments, the present invention provides vafidemstat, or a pharmaceutically acceptable salt or solvate thereof, for use in the treatment of a BPD patient by treating (e.g. alleviating or improving) one or more non-aggressive symptoms of BPD and by treating (e.g. reducing) aggression.

In some embodiments, the present invention provides a method for treating a BPD patient (preferably a human) by treating (e.g. alleviating or improving) one or more non-aggressive symptoms of BPD and by treating (e.g. reducing) aggression, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of a BPD patient by treating (e.g. alleviating or improving) one or more non-aggressive symptoms of BPD and by treating (e.g. reducing) aggression.

In some embodiments, the present invention provides the use of vafidemstat, or a pharmaceutically acceptable salt or solvate thereof, for the treatment of a BPD patient by treating (e.g. alleviating or improving) one or more non-aggressive symptoms of BPD and by treating (e.g. reducing) aggression.

In some embodiments, the present invention provides vafidemstat, or a pharmaceutically acceptable salt or solvate thereof, for use in the treatment of a BPD patient by treating (e.g. alleviating or improving) one or more core features of BPD and by treating (e.g. reducing) agitation.

In some embodiments, the present invention provides a method for treating a BPD patient (preferably a human) by treating (e.g. alleviating or improving) one or more core features of BPD and by treating (e.g. reducing) agitation, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of a BPD patient by treating (e.g. alleviating or improving) one or more core features of BPD and by treating (e.g. reducing) agitation.

In some embodiments, the present invention provides the use of vafidemstat, or a pharmaceutically acceptable salt or solvate thereof, for the treatment of a BPD patient by treating (e.g. alleviating or improving) one or more core features of BPD and by treating (e.g. reducing) agitation.

In some embodiments, the present invention provides vafidemstat, or a pharmaceutically acceptable salt or solvate thereof, for use in the treatment of a BPD patient by treating (e.g. alleviating or improving) one or more non-aggressive symptoms of BPD and by treating (e.g. reducing) agitation.

In some embodiments, the present invention provides a method for treating a BPD patient (preferably a human) by treating (e.g. alleviating or improving) one or more non-aggressive symptoms of BPD and by treating (e.g. reducing) agitation, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of a BPD patient by treating (e.g. alleviating or improving) one or more non-aggressive symptoms of BPD and by treating (e.g. reducing) agitation.

In some embodiments, the present invention provides the use of vafidemstat, or a pharmaceutically acceptable salt or solvate thereof, for the treatment of a BPD patient by treating (e.g. alleviating or improving) one or more non-aggressive symptoms of BPD and by treating (e.g. reducing) agitation.

In some embodiments, the present invention provides vafidemstat, or a pharmaceutically acceptable salt or solvate thereof, for use in the treatment of a BPD patient by treating (e.g. alleviating or improving) one or more core features of BPD and by treating (e.g. reducing) agitation and aggression.

In some embodiments, the present invention provides a method for treating a BPD patient (preferably a human) by treating (e.g. alleviating or improving) one or more core features of BPD and by treating (e.g. reducing) agitation and aggression, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of a BPD patient by treating (e.g. alleviating or improving) one or more core features of BPD and by treating (e.g. reducing) agitation and aggression.

In some embodiments, the present invention provides the use of vafidemstat, or a pharmaceutically acceptable salt or solvate thereof, for the treatment of a BPD patient by treating (e.g. alleviating or improving) one or more core features of BPD and by treating (e.g. reducing) agitation and aggression.

In some embodiments, the present invention provides vafidemstat, or a pharmaceutically acceptable salt or solvate thereof, for use in the treatment of a BPD patient by treating (e.g. alleviating or improving) one or more non-aggressive symptoms of BPD and by treating (e.g. reducing) agitation and aggression.

In some embodiments, the present invention provides a method for treating a BPD patient (preferably a human) by treating (e.g. alleviating or improving) one or more non-aggressive symptoms of BPD and by treating (e.g. reducing) agitation and aggression, the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of a BPD patient by treating (e.g. alleviating or improving) one or more non-aggressive symptoms of BPD and by treating (e.g. reducing) agitation and aggression.

In some embodiments, the present invention provides the use of vafidemstat, or a pharmaceutically acceptable salt or solvate thereof, for the treatment of a BPD patient by treating (e.g. alleviating or improving) one or more non-aggressive symptoms of BPD and by treating (e.g. reducing) agitation and aggression.

In some embodiments, the present invention provides vafidemstat, or a pharmaceutically acceptable salt or solvate thereof, for use in the treatment of one or more core features of BPD.

In some embodiments, the present invention provides a method for treating one or more core features of BPD in a patient (preferably a human), the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of one or more core features of BPD.

In some embodiments, the present invention provides the use of vafidemstat, or a pharmaceutically acceptable salt or solvate thereof, for the treatment of one or more core features of BPD.

In some embodiments, the present invention provides vafidemstat, or a pharmaceutically acceptable salt or solvate thereof, for use in the treatment of one or more non-aggressive symptoms of BPD.

In some embodiments, the present invention provides a method for treating one or more non-aggressive symptoms of BPD in a patient (preferably a human), comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of one or more non-aggressive symptoms of BPD.

In some embodiments, the present invention provides the use of vafidemstat, or a pharmaceutically acceptable salt or solvate thereof, for the treatment of one or more non-aggressive symptoms of BPD.

In some embodiments, the present invention provides vafidemstat, or a pharmaceutically acceptable salt or solvate thereof, for use in the treatment of one or more core features of BPD as well as agitation and/or aggression.

In some embodiments, the present invention provides a method for treating one or more core features of BPD as well as agitation and/or aggression in a patient (preferably a human), the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of one or more core features of BPD as well as agitation and/or aggression.

In some embodiments, the present invention provides the use of vafidemstat, or a pharmaceutically acceptable salt or solvate thereof, for the treatment of one or more core features of BPD as well as agitation and/or aggression.

In some embodiments, the present invention provides vafidemstat, or a pharmaceutically acceptable salt or solvate thereof, for use in the treatment of one or more non-aggressive symptoms of BPD as well as agitation and/or aggression.

In some embodiments, the present invention provides a method for treating one or more non-aggressive symptoms of BPD as well as agitation and/or aggression in a patient (preferably a human), the method comprising administering to the patient a therapeutically effective amount of vafidemstat, or a pharmaceutically acceptable salt or solvate thereof.

In some embodiments, the present invention provides the use of vafidemstat, or a pharmaceutically acceptable salt or solvate thereof, for the manufacture of a medicament for the treatment of one or more non-aggressive symptoms of BPD as well as agitation and/or aggression.

In some embodiments, the present invention provides the use of vafidemstat, or a pharmaceutically acceptable salt or solvate thereof, for the treatment of one or more non-aggressive symptoms of BPD as well as agitation and/or aggression.

Preferably, the KDM1A inhibitor for use in the herein described methods of treatment and uses, for example vafidemstat (or a pharmaceutically acceptable salt or solvate thereof), is administered orally. Exemplary formulations which can be administered via peroral ingestion are described in more detail further below.

As explained above, in preferred embodiments the present invention provides the compound vafidemstat, or a pharmaceutically acceptable salt or solvate thereof, for use in the treatment of BPD. Accordingly, the invention relates to the compound vafidemstat as a free base (in non-salt form) for use in the treatment of BPD and, furthermore, the invention also relates to a pharmaceutically acceptable salt or solvate of vafidemstat for use in the treatment of BPD.

Figure 2:
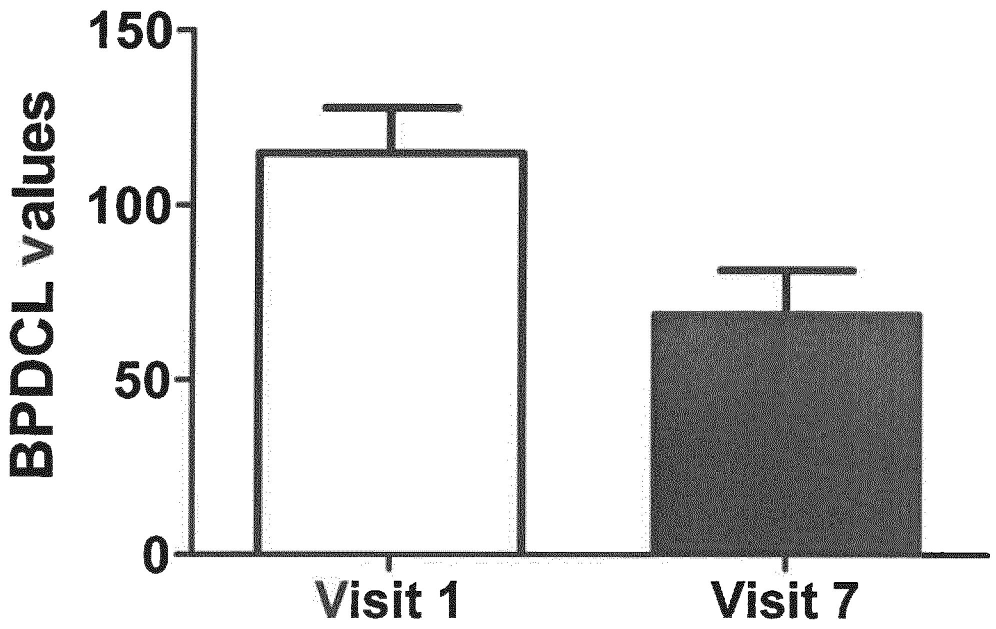
FIG. 2 shows the efficacy of the KDM1A inhibitor vafidemstat to treat BPD, as shown by a statistically significant reduction in the BPD Checklist (BPDCL) Total score from visit 1 (baseline, pre-treatment) to visit 7 (8 weeks treatment with vafidemstat), as described in more detail in Example 3. Data is represented as mean±SEM; p=0.0048.
Figure 3:
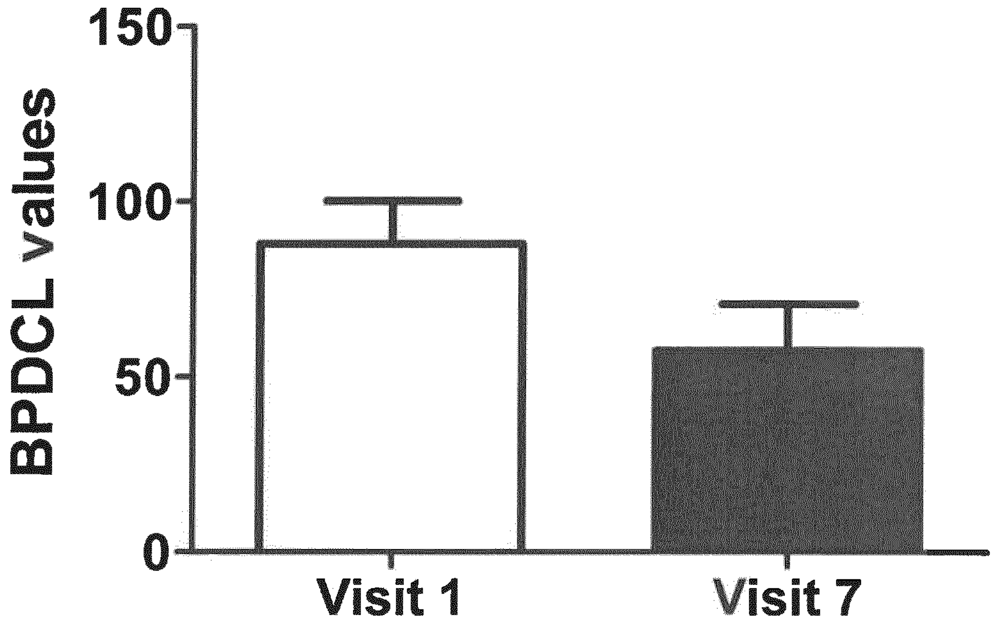
FIG. 3 shows treatment with vafidemstat produces a statistically significant reduction in the Non-aggression-related BPDCL domains combined score from visit 1 (baseline, pre-treatment) to visit 7 (8 weeks treatment with vafidemstat), as described in more detail in Example 3. Data is represented as mean±SEM; p=0.0234.

As illustrated in the Examples, it has been unexpectedly found in the context of the present invention that KDM1A inhibitors such as e.g. vafidemstat are useful to treat BPD. As part of a Phase IIa clinical trial evaluating the KDM1A inhibitor vafidemstat as a treatment for aggression in human patients with a range of CNS disorders, it has been shown that vafidemstat produces a significant reduction of aggressive behavior in BPD patients, as illustrated in Example 3 and FIG. 1. As shown in FIG. 1, treatment with the KDM1A inhibitor vafidemstat causes a statistically significant reduction in the score for aggression in said BPD patients, as shown by comparing the score after 8 weeks of treatment with the KDM1A inhibitor vafidemstat (score at visit 7) with the score at baseline, prior to starting treatment with vafidemstat (score at visit 1). Treatment efficacy in BPD patients is preferably assessed using a validated scale specifically designed for BPD, such as the Borderline Personality Disorder Checklist (BPDCL). As explained in greater detail in Example 3.3, the BPDCL scale includes the evaluation of aggression-related as well as non-aggression-related (i.e. aggression-independent) domains or symptoms of BPD. By assessing the effect of a treatment on the total BPDCL score, which includes aggression-related as well as non-aggression-related scores, and/or on a combined BPDCL score corresponding to those BPD domains unrelated to aggression, as detailed in Example 3.3, it is possible to evaluate the efficacy of a drug to treat BPD beyond (i.e. separate from) a specific effect on aggression. As illustrated in Example 3 and FIGS. 2 and 3, it has been surprisingly found that in addition to a therapeutic effect on aggression, treatment with the KDM1A inhibitor vafidemstat produces significant improvements on the overall BPD and on non-aggressive BPD features, as shown by statistically significant reductions in the BPDCL Total score (as illustrated in FIG. 2) and on the non-aggression combined score (as illustrated in FIG. 3) after 8 weeks of treatment. These results demonstrate that KDM1A inhibitors including vafidemstat have a broad therapeutic effect in BPD, having therapeutic effects in BPD patients beyond the treatment of aggression, and can thus be used to treat BPD, including core features of BPD as defined above.

KDM1A Inhibitors

As used herein, a KDM1A inhibitor is a compound which inhibits KDM1A, particularly human KDM1A.

All kinds of KDM1A inhibitors may be used in the methods and uses according to the invention.

Preferably, the KDM1A inhibitor to be used in the methods and uses according to the invention is a small molecule. Both irreversible and reversible KDM1A inhibitors have been reported and can be used in accordance with the present invention. Irreversible KDM1A inhibitors exert their inhibitory activity by becoming covalently bound to the FAD cofactor within the KDM1A active site and are generally based on a 2-cyclyl-cyclopropylamino moiety such as a 2-(hetero)arylcyclopropylamino moiety. Reversible inhibitors of KDM1A have also been disclosed.

Non-limiting examples of KDM1A inhibitors which can be used in accordance with the present invention are disclosed e.g. in: WO2010/043721, WO2010/084160, WO2011/035941, WO2011/042217, WO2011/131697, WO2012/013727, WO2012/013728, WO2012/045883, WO2013/057320, WO2013/057322, WO2010/143582, US2010-0324147, WO2011/022489, WO2011/131576, WO2012/034116, WO2012/135113, WO2013/022047, WO2013/025805, WO2014/058071, WO2014/084298, WO2014/086790, WO2014/164867, WO2014/205213, WO2015/021128, WO2015/031564, US2015-0065434, WO2007/021839, WO2008/127734, WO2015/089192, CN104119280, CN103961340, CN103893163, CN103319466, CN103054869, WO2015/123408, WO2015/123424, WO2015/123437, WO2015/123465, WO2015/156417, WO2015/181380, WO2016/123387, WO2016/130952, WO2016/172496, WO2016/177656, WO2017/027678, CN106045862, WO2012/071469, WO2013/033688, WO2014/085613, WO2015/120281, WO2015/134973, WO2015/168466, WO2015/200843, WO2016/003917, WO2016/004105, WO2016/007722, WO2016/007727, WO2016/007731, WO2016/007736, WO2016/034946, WO2016/037005, WO2016/161282, WO2017/004519, WO2017/027678, WO2017/079476, WO2017/079670, WO2017/090756, WO2017/109061, WO2017/116558, WO2017/114497, CN106432248, CN106478639, CN106831489, CN106928235, CN105985265, WO2017/149463, WO2017/157322, WO2017/195216, WO2017/198780, WO2017/215464, WO2018/081342, WO2018/081343, US2017-0283397, WO2019/009412, WO2018/234978, WO2018/226053, WO2018/216800, WO2018/213211, WO2018/137644, as well as

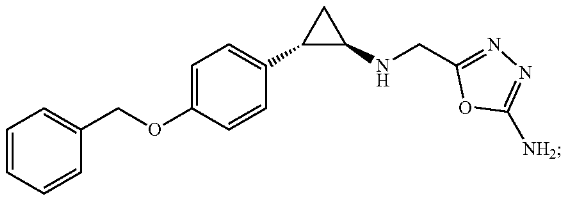

(vafidemstat)

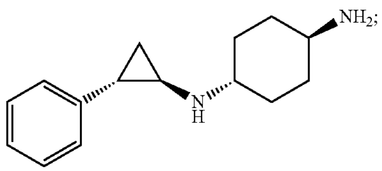

(iadademstat)

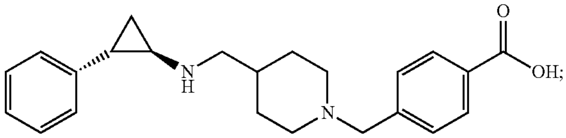

(GSK2879552)

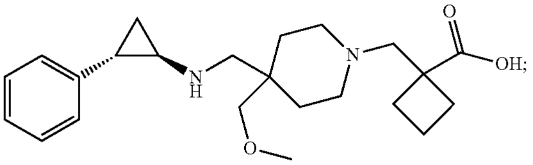

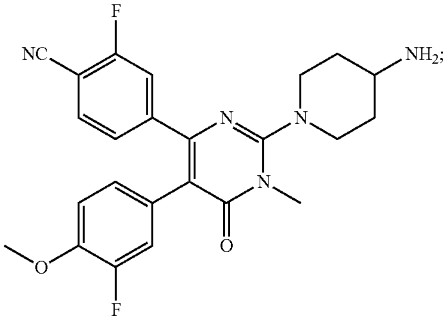

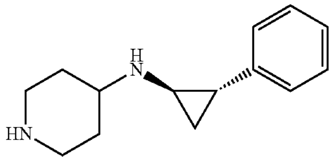

;

(GSK-LSD1)

-continued

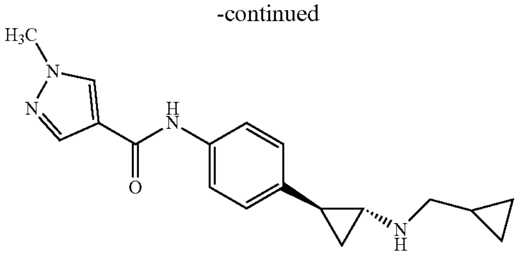

;

(T-3775440)

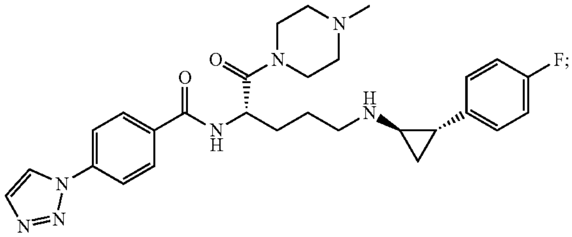

;

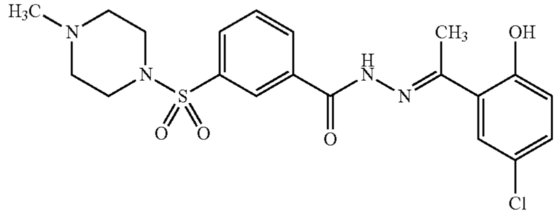

;

(seclidemstat)

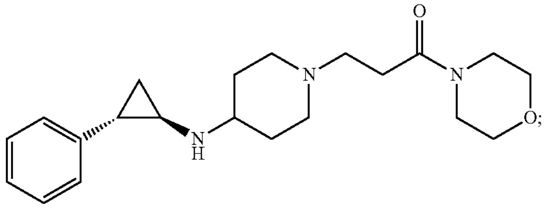

;

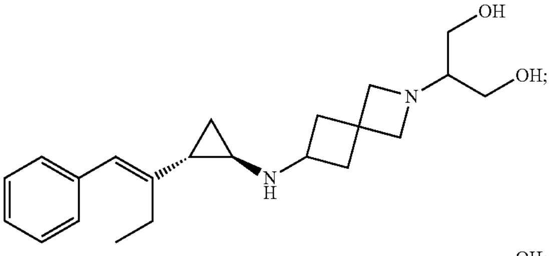

;

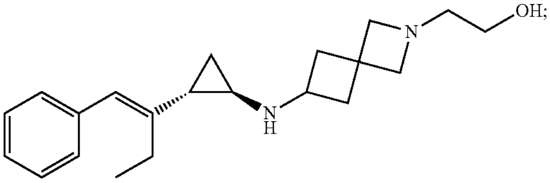

;

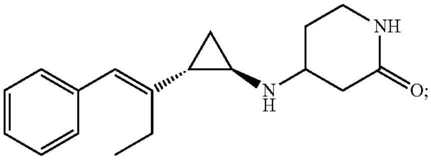 [SMILES: CC/C(=C\c1ccccc1)[C@@H]1C[C@H]1NC1CCNC(=O)C1]

;

5-{(1R,2R)-2-[(Cyclopropylmethyl)amino]cyclopropyl}-N-(tetrahydro-2H-pyran-4-yl)thiophene-3-carboxamide (TAK-418);

3-((1S,2R)-2-(cyclobutylamino)cyclopropyl)-N-(5-methyl-1,3,4-thiadiazol-2-yl)benzamide (T-448); or 3-((1S,2R)-2-(cyclopropylamino)cyclopropyl)-N-(5-methyl-1,3,4-thiadiazol-2-yl)benzamide;

including any optically active stereoisomer thereof, or any pharmaceutically acceptable salt or solvate thereof.

Any one of the above-depicted compounds comprising a 1,2-substituted cyclopropyl ring can be employed in the form of the corresponding trans-isomer (wherein the two substituents at the cyclopropyl ring are in trans-configuration), or in the form of any one of the respective specific trans-isomers (wherein the two substituents at the cyclopropyl ring have the same absolute configuration as shown in the drawn structure; or wherein the two substituents at the cyclopropyl ring each have the opposite absolute configuration as shown in the drawn structure).

Further non-limiting examples of KDM1A inhibitors to be used in accordance with the present invention are disclosed e.g. in: K Taeko et al, Bioorg Med Chem Lett 2015, 25(9):1925-8. doi: 10.1016/j.bmcl.2015.03.030. Epub 2015 Mar. 20, PMID: 25827526; S Valente et al, Eur J Med Chem. 2015, 94:163-74. doi: 10.1016/j.ejmech.2015.02.060. Epub 2015 Mar. 3, PMID:25768700; MN Ahmed Khan et al Med. Chem. Commun., 2015, 6, 407-412, DOI: 10.1039/C4MD00330F epub 29 Sep. 2014; M Pieroni et al, Eur J Med Chem. 2015; 92:377-386. doi: 10.1016/j.ejmech.2014.12.032. Epub 2015 Jan. 7. PMID:25585008; V Rodriguez et al, Med. Chem. Commun., 2015, 6, 665-670 DOI: 10.1039/C4MD00507D, Epub 23 Dec. 2014; P Vianello et al, Eur J Med Chem. 2014, 86:352-63. doi: 10.1016/j.ejmech.2014.08.068. Epub 2014 Aug. 27; D P Mould et al, Med. Res. Rev., 2015, 35:586-618. doi: 10.1002/med.21334, epub 24 Nov. 2014; LY Ma et al, 2015, 58(4):1705-16. doi: 10.1021/acs.jmedchem.5b00037. Epub 2015 Feb. 6; S L Nowotarski et al, 2015, 23(7):1601-12. doi: 10.1016/j.bmc.2015.01.049. Epub 2015 Feb. 7. PMID: 25725609; C J Kutz et al Medchemcomm. 2014, 5(12): 1863-1870 PMID: 25580204; C Zhou et al, Chemical Biology & Drug Design, 2015, 85(6):659-671. doi:10.1111/cbdd.12461, epub 22 Dec. 2014; P Prusevich et al, ACS Chem Biol. 2014, 9(6):1284-93. doi: 10.1021/cb500018s. Epub 2014 Apr. 7; B Dulla et al, Org Biomol Chem 2013, 11, 3103-3107, doi: 10.1039/c3ob40217g; J R Hitchin et al, MedChemCommun, 2013, 4, 1513-1522 DOI: 10.1039/c3md00226h; and Y Zhou et al, Biorg Med Chem Lett, 2015, online publication 20 Jun. 2015, doi:10.1016/j.bmcl.2015.06.054. Irreversible KDM1A inhibitors that can be used in the methods/uses of the invention include, without limitation, any one of the compounds disclosed in: WO2010/043721, WO2010/084160, WO2011/035941, WO2011/042217, WO2011/131697, WO2012/013727, WO2012/013728, WO2012/045883, WO2013/057320, WO2013/057322, WO2010/143582, US2010-0324147, WO2011/131576, WO2012/135113, WO2013/022047, WO2014/058071, WO2014/084298, WO2014/086790, WO2014/164867, WO2015/021128; WO2015/123408, WO2015/123424, WO2015/123437, WO2015/123465, WO2015/156417, WO2015/181380, WO2016/123387, WO2016/130952, WO2016/172496, WO2016/177656, WO2017/027678, CN106045862, WO2014/164867 WO2017/027678, WO2017/079476, WO2017/109061, WO2017/116558, WO2017/114497, CN106831489; WO2018/137644, WO2018/226053, WO2019/009412, K Taeko et al, Bioorg Med Chem Lett. 2015, 25(9):1925-8. doi: 10.1016/j.bmcl.2015.03.030. Epub 2015 Mar. 20, PMID: 25827526; S Valente et al, Eur J Med Chem. 2015, 94:163-74. doi: 10.1016/j.ejmech.2015.02.060. Epub 2015 Mar. 3, PMID:25768700; MN Ahmed Khan et al Med. Chem. Commun., 2015, 6, 407-412, DOI: 10.1039/

C4MD00330F epub 29 Sep. 2014; M Pieroni et al, Eur J Med Chem. 2015; 92:377-386. doi: 10.1016/j.ejmech.2014.12.032. Epub 2015 Jan. 7. PMID:25585008; V Rodriguez et al, Med. Chem. Commun., 2015, 6, 665-670 DOI: 10.1039/C4MD00507D, Epub 23 Dec. 2014; or P Vianello et al, Eur J Med Chem. 2014, 86:352-63. doi: 10.1016/j.ejmech.2014.08.068. Epub 2014 Aug. 27, as well as

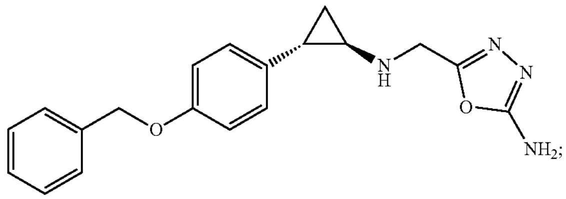

(vafidemstat)

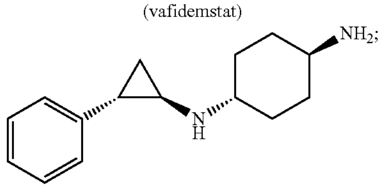

(iadademstat)

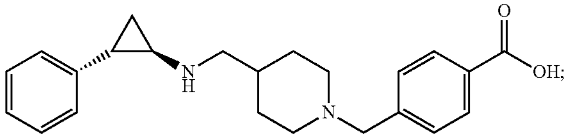

(GSK2879552)

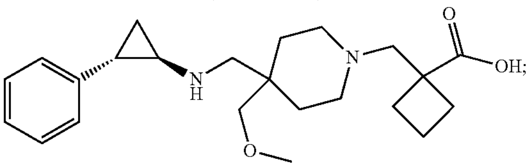

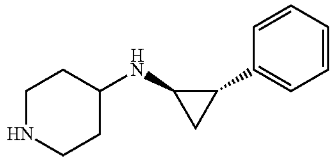
;

(GSK-LSD1)

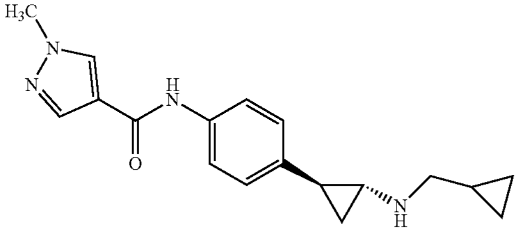
;

(T-3775440)

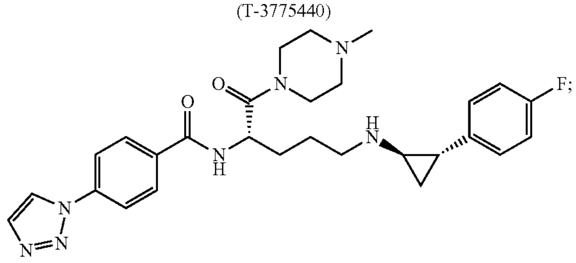

-continued

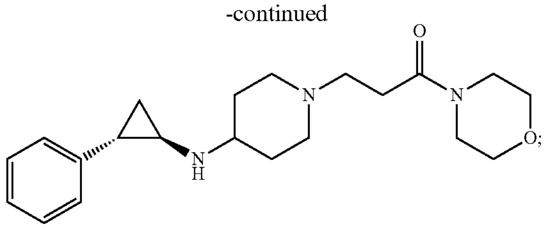

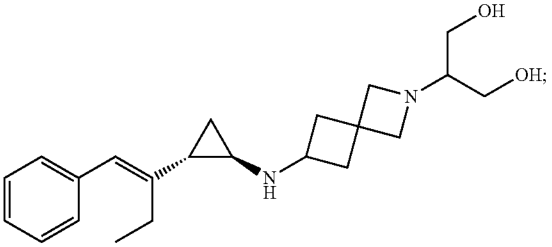

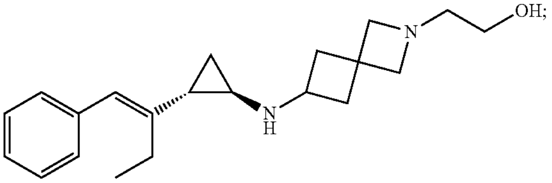

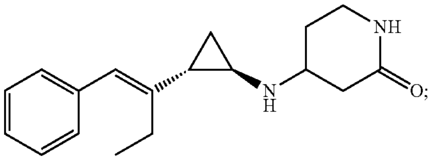 [SMILES: CC/C(=C\c1ccccc1)[C@@H]1C[C@H]1NC1CCNC(=O)C1]

5-{(1R,2R)-2-[(Cyclopropylmethyl)amino]cyclopropyl}-N-(tetrahydro-2H-pyran-4-yl)thiophene-3-carboxamide (TAK-418);

3-((1S,2R)-2-(cyclobutylamino)cyclopropyl)-N-(5-methyl-1,3,4-thiadiazol-2-yl)benzamide (T-448); or 3-((1S,2R)-2-(cyclopropylamino)cyclopropyl)-N-(5-methyl-1,3,4-thiadiazol-2-yl)benzamide;

including any optically active stereoisomer thereof, or any pharmaceutically acceptable salt or solvate thereof.

Any one of the above-depicted compounds comprising a 1,2-substituted cyclopropyl ring can be employed in the form of the corresponding trans-isomer (wherein the two substituents at the cyclopropyl ring are in trans-configuration), or in the form of any one of the respective specific trans-isomers (wherein the two substituents at the cyclopropyl ring have the same absolute configuration as shown in the drawn structure; or wherein the two substituents at the cyclopropyl ring each have the opposite absolute configuration as shown in the drawn structure).

Reversible KDM1A inhibitors that can be used in the methods/uses of the invention include, without limitation, any one of the compounds disclosed in WO2007/021839, WO2008/127734, WO2011/022489, WO2012/034116, WO2012/071469, WO2013/025805, US2015/0065434, WO2013/033688, CN103054869, CN103319466, WO2014/085613, CN103893163A, CN103961340, WO2014/205213, WO2015/031564, WO2015/089192, WO2015/120281, WO2015/134973, WO2015/168466, WO2015/200843, WO2016/003917, WO2016/004105, WO2016/007722, WO2016/007727, WO2016/007731, WO2016/007736, WO2016/034946, WO2016/037005, WO2016/161282, WO2017/004519, WO2017/079670, WO2017/090756, CN106432248, CN106478639, CN106928235, WO2018/234978, WO2018/216800, WO2018/213211, as well as

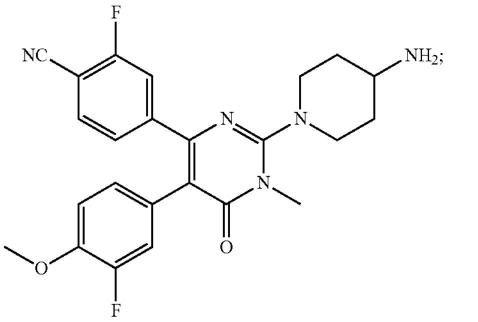

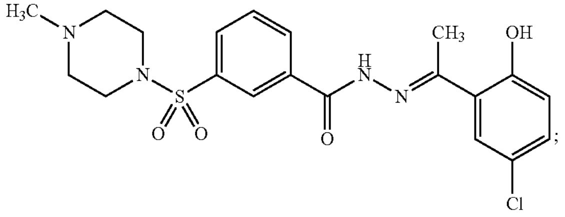

(seclidemstat)

including any optically active stereoisomer thereof, or any pharmaceutically acceptable salt or solvate thereof. In some embodiments, in the methods and uses according to the invention, the KDM1A inhibitor is an irreversible KDM1A inhibitor, preferably a 2-(hetero)arylcyclopropylamino KDM1A inhibitor. As used herein, a “2-(hetero)arylcyclopropylamino KDM1A inhibitor” or a “2-(hetero)arylcyclopropylamino compound” means a KDM1A inhibitor whose chemical structure comprises a cyclopropyl ring substituted at position 1 with an amino group, which is optionally substituted, and substituted at position 2 with an aryl or heteroaryl group (wherein the aryl or heteroaryl group is optionally substituted).

The ability of a compound to inhibit KDM1A can be tested in vitro using any method to determine KDM1A inhibition known in the art, for example the method disclosed in Example 2.

A particularly preferred KDM1A inhibitor for use in the methods and uses according to the invention is vafidemstat (i.e. 5-((((1R,2S)-2-(4-(benzyloxy)phenyl)cyclopropyl)amino)methyl)-1,3,4-oxadiazol-2-amine), or a pharmaceutically acceptable salt or solvate thereof.

Other KDM1A inhibitors that can be used in the methods and uses of the invention include:

5-{(1R,2R)-2-[(Cyclopropylmethyl)amino]cyclopropyl}-N-(tetrahydro-2H-pyran-4-yl)thiophene-3-carboxamide (TAK-418);

3-((1S,2R)-2-(cyclobutylamino)cyclopropyl)-N-(5-methyl-1,3,4-thiadiazol-2-yl)benzamide (T-448);

3-((1S,2R)-2-(cyclopropylamino)cyclopropyl)-N-(5-methyl-1,3,4-thiadiazol-2-yl)benzamide;

(trans)-N1-((1R,2S)-2-phenylcyclopropyl)cyclohexane-1,4-diamine (iadademstat);

(cis)-N1-((1S,2R)-2-phenylcyclopropyl)cyclohexane-1,4-diamine;

(trans)-N1-((1S,2R)-2-phenylcyclopropyl)cyclohexane-1,4-diamine;

(cis)-N1-((1R,2S)-2-phenylcyclopropyl)cyclohexane-1,4-diamine;

N1-((trans)-2-(thiazol-5-yl)cyclopropyl)cyclohexane-1,4-diamine;

N1-((trans)-2-(pyridin-3-yl)cyclopropyl)cyclohexane-1,4-diamine;

N1-((trans)-2-(6-(3-(tifluoromethyl)phenyl)pyridin-3-yl)cyclopropyl)cyclohexane-1,4-diamine;

N1-((trans)-2-(3'-(trifluoromethyl)-[1,1'-biphenyl]-4-yl)cyclopropyl)cyclohexane-1,4-diamine;

N1-((trans)-2-(4-(benzyloxy)phenyl)cyclopropyl)cyclohexane-1,4-diamine;

4-(((trans)-2-(6-(3-(trifluoromethyl)phenyl)pyridin-3-yl)cyclopropyl)amino)cyclohexanol;

4-(((trans)-2-(6-(3-(trifluoromethyl)phenyl)pyridin-3-yl)cyclopropyl)amino)cyclohexanecarboxamide;

N-(4-(((trans)-2-(6-(3-(trifluoromethyl)phenyl)pyridin-3-yl)cyclopropyl)amino)cyclohexyl)acetamide;

N-(4-(((trans)-2-(6-(3-(trifluoromethyl)phenyl)pyridin-3-yl)cyclopropyl)amino)cyclohexyl)methanesulfonamide;

(R)-1-(4-(((trans)-2-phenylcyclopropyl)amino)cyclohexyl)pyrrolidin-3-amine;

N1-((trans)-2-(4'-chloro-[1,1'-biphenyl]-4-yl)cyclopropyl)cyclohexane-1,4-diamine;

N1-((trans)-2-(3'-chloro-[1,1'-biphenyl]-4-yl)cyclopropyl)cyclohexane-1,4-diamine;

4'-((trans)-2-((4-aminocyclohexyl)amino)cyclopropyl)-[1,1'-biphenyl]-3-ol;

N-(4'-((trans)-2-((4-aminocyclohexyl)amino)cyclopropyl)-[1,1'-biphenyl]-3-yl)methanesulfonamide;

N1-((trans)-2-(4-((2-fluorobenzyl)oxy)phenyl)cyclopropyl)cyclohexane-1,4-diamine;

N1-((trans)-2-(4-((3-fluorobenzyl)oxy)phenyl)cyclopropyl)cyclohexane-1,4-diamine;

N1-((trans)-2-(4-((4-fluorobenzyl)oxy)phenyl)cyclopropyl)cyclohexane-1,4-diamine;

N1-methyl-N4-((trans)-2-phenylcyclopropyl)cyclohexane-1,4-diamine;

N1-methyl-N4-((trans)-2-(3'-(trifluoromethyl)-[1,1'-biphenyl]-4-yl)cyclopropyl)cyclohexane-1,4-diamine;

N1-((trans)-2-(4-(benzyloxy)phenyl)cyclopropyl)-N4-methylcyclohexane-1,4-diamine;

N1-((trans)-2-phenylcyclopropyl)cyclobutane-1,3-diamine;

N1-((trans)-2-(3'-(trifluoromethyl)-[1,1'-biphenyl]-4-yl)cyclopropyl)cyclobutane-1,3-diamine;

N1-((trans)-2-(4-(benzyloxy)phenyl)cyclopropyl)cyclobutane-1,3-diamine;

N1-((trans)-2-phenylcyclopropyl)-2,3-dihydro-1H-indene-1,3-diamine;

N1-((trans)-2-(3'-(trifluoromethyl)-[1,1'-biphenyl]-4-yl)cyclopropyl)-2,3-dihydro-1H-indene-1,3-diamine;

N1-((trans)-2-(4-(benzyloxy)phenyl)cyclopropyl)-2,3-dihydro-1H-indene-1,3-diamine;

N1-((trans)-2-fluoro-2-phenylcyclopropyl)cyclohexane-1,4-diamine;

N1-((1S,2S)-2-fluoro-2-phenylcyclopropyl)cyclohexane-1,4-diamine;

N1-((1R,2R)-2-fluoro-2-phenylcyclopropyl)cyclohexane-1,4-diamine;

1-methyl-N4-((trans)-2-phenylcyclopropyl)cyclohexane-1,4-diamine;

4-(aminomethyl)-N-((trans)-2-phenylcyclopropyl)cyclohexanamine;

N1-((trans)-2-phenylcyclopropyl)cyclohexane-1,3-diamine;

N1-((cis)-2-phenylcyclopropyl)cyclohexane-1,4-diamine;

Tert-butyl (4-(((trans)-2-phenylcyclopropyl)amino)cyclohexyl)carbamate;

1-ethyl-3-(4-(((trans)-2-phenylcyclopropyl)amino)cyclohexyl)urea;

4-morpholino-N-((trans)-2-phenylcyclopropyl)cyclohexanamine;

N1-((trans)-2-(4-bromophenyl)cyclopropyl)cyclohexane-1,4-diamine;

N1-(2-(o-tolyl)cyclopropyl)cyclohexane-1,4-diamine;
N1-(2-(4-(trifluoromethyl)phenyl)cyclopropyl)cyclohexane-1,4-diamine;
N1-(2-(4-methoxyphenyl)cyclopropyl)cyclohexane-1,4-diamine;
4-(2-((4-aminocyclohexyl)amino)cyclopropyl)phenol;
N1-(2-(2-fluorophenyl)cyclopropyl)cyclohexane-1,4-diamine;
N1-(2-(3,4-difluorophenyl)cyclopropyl)cyclohexane-1,4-diamine;
N1-(2-(naphthalen-2-yl)cyclopropyl)cyclohexane-1,4-diamine;
N1-(2-methyl-2-phenylcyclopropyl)cyclohexane-1,4-diamine;
(R)-1-(4-(((trans)-2-(3'-(trifluoromethyl)-[1,1'-biphenyl]-4-yl)cyclopropyl) amino)cyclohexyl)pyrrolidin-3-amine;
(Cis)-N1-((1S,2R)-2-(3'-(trifluoromethyl)-[1,1'-biphenyl]-4-yl)cyclopropyl)cyclohexane-1,4-diamine;
(Trans)-N1-((1S,2R)-2-(3'-(trifluoromethyl)-[1,1'-biphenyl]-4-yl)cyclo-propyl)cyclohexane-1,4-diamine;
(Cis)-N1-((1R,2S)-2-(3'-(trifluoromethyl)-[1,1'-biphenyl]-4-yl)cyclo-propyl)cyclohexane-1,4-diamine;
(Trans)-N1-((1R,2S)-2-(3'-(trifluoromethyl)-[1,1'-biphenyl]-4-yl)cyclo-propyl)cyclohexane-1,4-diamine;
N1-((trans)-2-(4-cyclopropylphenyl)cyclopropyl)cyclohexane-1,4-diamine;
N1-((trans)-2-(4-(pyridin-3-yl)phenyl)cyclopropyl)cyclohexane-1,4-diamine;
N1-((trans)-2-(4-(1H-indazol-6-yl)phenyl)cyclopropyl)cyclohexane-1,4-diamine;
N1-((trans)-2-(4-(1H-pyrazol-5-yl)phenyl)cyclopropyl)cyclohexane-1,4-diamine;
3-(5-((trans)-2-((4-aminocyclohexyl)amino)cyclopropyl) thiophen-2-yl)phenol;
3-(5-((trans)-2-((4-aminocyclohexyl)amino)cyclopropyl) thiazol-2-yl)phenol;
3-(5-((trans)-2-((4-aminocyclohexyl)amino)cyclopropyl) pyridin-2-yl)-5-methoxybenzonitrile;
5-(5-((trans)-2-((4-aminocyclohexyl)amino)cyclopropyl) pyridin-2-yl)-2-methylphenol;
N-(4'-((trans)-2-((4-aminocyclohexyl)amino)cyclopropyl)-6-methoxy-[1,1'-biphenyl]-3-yl)methanesulfonamide;
N-(3-(5-((trans)-2-((4-aminocyclohexyl)amino)cyclopropyl)thiazol-2-yl)phenyl)-2-cyanobenzenesulfonamide;
N-(4'-((trans)-2-((4-aminocyclohexyl)amino)cyclopropyl)-[1,1'-biphenyl]-3-yl)-2-cyanobenzenesulfonamide;
6-amino-N-(4'-((trans)-2-((4-aminocyclohexyl)amino)cyclopropyl)-[1,1'-biphenyl]-3-yl)pyridine-3-sulfonamide;
N-(4'-((trans)-2-((4-aminocyclohexyl)amino)cyclopropyl)-[1,1'-biphenyl]-3-yl)piperazine-1-sulfonamide;
N1-((cis)-2-fluoro-2-phenylcyclopropyl)cyclohexane-1,4-diamine;
N1-((trans)-2-(4-((3-(piperazin-1-yl)benzyl)oxy)phenyl)cyclopropyl)cyclohexane-1,4-diamine;
N1-((trans)-2-(4-(pyridin-3-ylmethoxy)phenyl)cyclopropyl) cyclohexane-1,4-diamine;
N1-((trans)-2-(6-((3-methylbenzyl)amino)pyridin-3-yl)cyclopropyl)cyclohexane-1,4-diamine;
3-((5-((trans)-2-((4-aminocyclohexyl)amino)cyclopropyl) pyridin-2-yl) amino)benzonitrile;
N1-((trans)-2-(naphthalen-2-yl)cyclopropyl)cyclohexane-1,4-diamine;
N1-((trans)-2-(o-tolyl)cyclopropyl)cyclohexane-1,4-diamine;
N1-((trans)-2-(4-(trifluoromethyl)phenyl)cyclopropyl)cyclohexane-1,4-diamine;
N1-((trans)-2-(4-methoxyphenyl)cyclopropyl)cyclohexane-1,4-diamine;
N1-((trans)-2-(2-fluorophenyl)cyclopropyl)cyclohexane-1,4-diamine;
N1-((trans)-2-(3,4-difluorophenyl)cyclopropyl)cyclohexane-1,4-diamine;
N1-((trans)-2-methyl-2-phenylcyclopropyl)cyclohexane-1,4-diamine;
(cis)-N1-((1S,2R)-2-(pyridin-3-yl)cyclopropyl)cyclohexane-1,4-diamine;
(trans)-N1-((1R,2S)-2-(pyridin-3-yl)cyclopropyl)cyclohexane-1,4-diamine;
(cis)-N1-((1R,2S)-2-(pyridin-3-yl)cyclopropyl)cyclohexane-1,4-diamine;
(trans)-N1-((1S,2R)-2-(pyridin-3-yl)cyclopropyl)cyclohexane-1,4-diamine;
(cis)-N1-((1S,2R)-2-phenylcyclopropyl)cyclobutane-1,3-diamine;
(trans)-N1-((1R,2S)-2-phenylcyclopropyl)cyclobutane-1,3-diamine;
(cis)-N1-((1R,2S)-2-phenylcyclopropyl)cyclobutane-1,3-diamine;
(trans)-N1-((1S,2R)-2-phenylcyclopropyl)cyclobutane-1,3-diamine;
(cis)-N1-((1S,2R)-2-(3,4-difluorophenyl)cyclopropyl)cyclohexane-1,4-diamine;
(trans)-N1-((1R,2S)-2-(3,4-difluorophenyl)cyclopropyl)cyclohexane-1,4-diamine;
(cis)-N1-((1R,2S)-2-(3,4-difluorophenyl)cyclopropyl)cyclohexane-1,4-diamine;
(trans)-N1-((1S,2R)-2-(3,4-difluorophenyl)cyclopropyl)cyclohexane-1,4-diamine;
(cis)-N1-((1S,2R)-2-(naphthalen-2-yl)cyclopropyl)cyclohexane-1,4-diamine;
(trans)-N1-((1R,2S)-2-(naphthalen-2-yl)cyclopropyl)cyclohexane-1,4-diamine;
(cis)-N1-((1R,2S)-2-(naphthalen-2-yl)cyclopropyl)cyclohexane-1,4-diamine;
(trans)-N1-((1S,2R)-2-(naphthalen-2-yl)cyclopropyl)cyclohexane-1,4-diamine;
(cis)-N1-((1S,2R)-2-(4-(1H-pyrazol-5-yl)phenyl)cyclopropyl)cyclohexane-1,4-diamine;
(trans)-N1-((1R,2S)-2-(4-(1H-pyrazol-5-yl)phenyl)cyclopropyl)cyclohexane-1,4-diamine;
(cis)-N1-((1R,2S)-2-(4-(1H-pyrazol-5-yl)phenyl)cyclopropyl)cyclohexane-1,4-diamine;
(trans)-N1-((1S,2R)-2-(4-(1H-pyrazol-5-yl)phenyl)cyclopropyl)cyclohexane-1,4-diamine;
N-(4'-((1R,2S)-2-(((cis)-4-aminocyclohexyl)amino)cyclopropyl)-[1,1'-biphenyl]-3-yl)piperazine-1-sulfonamide;
N-(4'-((1S,2R)-2-(((trans)-4-aminocyclohexyl)amino)cyclopropyl)-[1,1'-biphenyl]-3-yl)piperazine-1-sulfonamide;
N-(4'-((1S,2R)-2-(((cis)-4-aminocyclohexyl)amino)cyclopropyl)-[1,1'-biphenyl]-3-yl)piperazine-1-sulfonamide;
N-(4'-((1R,2S)-2-(((trans)-4-aminocyclohexyl)amino)cyclopropyl)-[1,1'-biphenyl]-3-yl)piperazine-1-sulfonamide;
(cis)-N1-((1S,2R)-2-(4-((2-fluorobenzyl)oxy)phenyl)cyclopropyl)cyclohexane-1,4-diamine;
(trans)-N1-((1R,2S)-2-(4-((2-fluorobenzyl)oxy)phenyl)cyclopropyl)cyclohexane-1,4-diamine;
(cis)-N1-((1R,2S)-2-(4-((2-fluorobenzyl)oxy)phenyl)cyclopropyl)cyclohexane-1,4-diamine;
(trans)-N1-((1S,2R)-2-(4-((2-fluorobenzyl)oxy)phenyl)cyclopropyl)cyclohexane-1,4-diamine;
N-((trans)-2-phenylcyclopropyl)piperidin-4-amine;

N-((1S,2R)-2-phenylcyclopropyl)piperidin-4-amine;
N-((1R,2S)-2-phenylcyclopropyl)piperidin-4-amine;
N-((trans)-2-(4-(benzyloxy)phenyl)cyclopropyl)piperidin-4-amine;
N-((trans)-2-(6-(3-(trifluoromethyl)phenyl)pyridin-3-yl)cyclopropyl)tetrahydro-2H-pyran-4-amine;
N-((trans)-2-(pyridin-3-yl)cyclopropyl)piperidin-4-amine;
N-((trans)-2-(thiazol-5-yl)cyclopropyl)piperidin-4-amine;
N-((trans)-2-(3'-(trifluoromethyl)-[1,1'-biphenyl]-4-yl)cyclopropyl)piperidin-4-amine;
N-((trans)-2-phenylcyclopropyl)piperidin-3-amine;
N-((trans)-2-(3'-(trifluoromethyl)-[1,1'-biphenyl]-4-yl)cyclopropyl)piperidin-3-amine;
N-((trans)-2-(4-(benzyloxy)phenyl)cyclopropyl)piperidin-3-amine;
N-((trans)-2-phenylcyclopropyl)pyrrolidin-3-amine;
N-((trans)-2-(3'-(trifluoromethyl)-[1,1'-biphenyl]-4-yl)cyclopropyl)pyrrolidin-3-amine;
N-((trans)-2-(4-(benzyloxy)phenyl)cyclopropyl)pyrrolidin-3-amine;
N-((trans)-2-phenylcyclopropyl)azetidin-3-amine;
N-((trans)-2-(3'-(trifluoromethyl)-[1,1'-biphenyl]-4-yl)cyclopropyl)azetidin-3-amine;
N-((trans)-2-(4-(benzyloxy)phenyl)cyclopropyl)azetidin-3-amine;
N-((trans)-2-phenylcyclopropyl)azepan-3-amine;
N-((trans)-2-phenylcyclopropyl)-8-azabicyclo[3.2.1]octan-3-amine;
N-((trans)-2-phenylcyclopropyl)-3-azabicyclo[3.2.1]octan-8-amine;
N-((trans)-2-phenylcyclopropyl)decahydroquinolin-4-amine;
N-((trans)-2-phenylcyclopropyl)-1,2,3,4-tetrahydroquinolin-4-amine;
N-((trans)-2-phenylcyclopropyl)-3-azaspiro[5.5]undecan-9-amine;
N-((trans)-2-phenylcyclopropyl)-2-azaspiro[4.5]decan-8-amine;
N-((trans)-2-phenylcyclopropyl)-2,3-dihydrospiro[indene-1,4'-piperidin]-3-amine;
N-((1S,2R)-2-(4-(benzyloxy)phenyl)cyclopropyl)piperidin-4-amine;
N-((1R,2S)-2-(4-(benzyloxy)phenyl)cyclopropyl)piperidin-4-amine;
N-((1S,2R)-2-(pyridin-3-yl)cyclopropyl)piperidin-4-amine;
N-((1R,2S)-2-(pyridin-3-yl)cyclopropyl)piperidin-4-amine;
N-((1S,2S)-2-(thiazol-5-yl)cyclopropyl)piperidin-4-amine;
N-((1R,2R)-2-(thiazol-5-yl)cyclopropyl)piperidin-4-amine;
N-((1S,2R)-2-(3'-(trifluoromethyl)-[1,1'-biphenyl]-4-yl)cyclopropyl)piperidin-4-amine;
N-((1R,2S)-2-(3'-(trifluoromethyl)-[1,1'-biphenyl]-4-yl)cyclopropyl)piperidin-4-amine;
N-((trans)-2-phenylcyclopropyl)-7-azaspiro[3.5]nonan-2-amine;
N-(2-(o-tolyl)cyclopropyl)piperidin-4-amine;
N-(2-(2-fluorophenyl)cyclopropyl)piperidin-4-amine;
N-(2-(3,4-difluorophenyl)cyclopropyl)piperidin-4-amine;
N-(2-(4-methoxyphenyl)cyclopropyl)piperidin-4-amine;
N-(2-(naphthalen-2-yl)cyclopropyl)piperidin-4-amine;
N-(2-methyl-2-phenylcyclopropyl)piperidin-4-amine;
N-(6-methoxy-4'-((trans)-2-(piperidin-4-ylamino)cyclopropyl)-[1,1'-biphenyl]-3-yl)methanesulfonamide;
N-(4'-((trans)-2-(piperidin-4-ylamino)cyclopropyl)-[1,1'-biphenyl]-3-yl)propane-2-sulfonamide;
1-(methylsulfonyl)-N-((trans)-2-phenylcyclopropyl)piperidin-4-amine;

1-(4-(((trans)-2-(4-bromophenyl)cyclopropyl)amino)piperidin-1-yl)ethanone;
4-(((trans)-2-(4-bromophenyl)cyclopropyl)amino)piperidine-1-carboxamide;
N-((trans)-2-(4-bromophenyl)cyclopropyl)tetrahydro-2H-pyran-4-amine;
2,2,6,6-tetramethyl-N-((trans)-2-phenylcyclopropyl)piperidin-4-amine;
1-methyl-N-((trans)-2-phenylcyclopropyl)piperidin-4-amine;
1-isopropyl-N-((trans)-2-phenylcyclopropyl)piperidin-4-amine;
N-((trans)-2-phenylcyclopropyl)-1-(2,2,2-trifluoroethyl)piperidin-4-amine;
N-((trans)-2-phenylcyclopropyl)-1-(pyridin-4-yl)piperidin-4-amine;
4-(((trans)-2-(4-bromophenyl)cyclopropyl)amino)tetrahydro-2H-thiopyran 1,1-dioxide;
N-((trans)-2-fluoro-2-phenylcyclopropyl)piperidin-4-amine;
N-((1S,2S)-2-fluoro-2-phenylcyclopropyl)piperidin-4-amine;
N-((1R,2R)-2-fluoro-2-phenylcyclopropyl)piperidin-4-amine;
N-((trans)-2-(naphthalen-2-yl)cyclopropyl)piperidin-4-amine;
N-((trans)-2-methyl-2-phenylcyclopropyl)piperidin-4-amine;
N-((trans)-2-(o-tolyl)cyclopropyl)piperidin-4-amine;
N-((trans)-2-(2-fluorophenyl)cyclopropyl)piperidin-4-amine;
N-((trans)-2-(3,4-difluorophenyl)cyclopropyl)piperidin-4-amine;
N-((trans)-2-(4-methoxyphenyl)cyclopropyl)piperidin-4-amine;
(Trans)-2-phenyl-N-(piperidin-4-ylmethyl)cyclopropanamine;
(Trans)-2-phenyl-N-(2-(piperidin-4-yl)ethyl)cyclopropanamine;
(Trans)-2-phenyl-N-(2-(tetrahydro-2H-pyran-4-yl)ethyl)cyclopropanamine;
(Trans)-2-(4'-chloro-[1,1'-biphenyl]-4-yl)-N-(2-(tetrahydro-2H-pyran-4-yl)ethyl)cyclopropanamine;
(Trans)-N-(piperidin-4-ylmethyl)-2-(pyridin-3-yl)cyclopropanamine;
(Trans)-N-(piperidin-4-ylmethyl)-2-(thiazol-5-yl)cyclopropanamine;
(Trans)-N-(piperidin-4-ylmethyl)-2-(3'-(trifluoromethyl)-[1,1'-biphenyl]-4-yl)cyclopropanamine;
(Trans)-2-(4-(benzyloxy)phenyl)-N-(piperidin-4-ylmethyl)cyclopropanamine;
(Trans)-N-(2-(piperidin-4-yl)ethyl)-2-(pyridin-3-yl)cyclopropanamine;
(Trans)-N-(2-(piperidin-4-yl)ethyl)-2-(thiazol-5-yl)cyclopropanamine;
(Trans)-N-(2-(piperidin-4-yl)ethyl)-2-(3'-(trifluoromethyl)-[1,1'-biphenyl]-4-yl)cyclopropanamine;
(Trans)-2-(4-(benzyloxy)phenyl)-N-(2-(piperidin-4-yl)ethyl)cyclopropanamine;
(1S,2R)-2-phenyl-N-(piperidin-4-ylmethyl)cyclopropanamine;
(1R,2S)-2-phenyl-N-(piperidin-4-ylmethyl)cyclopropanamine;
(1S,2R)-2-phenyl-N-(2-(piperidin-4-yl)ethyl)cyclopropanamine;
(1R,2S)-2-phenyl-N-(2-(piperidin-4-yl)ethyl)cyclopropanamine;

(1S,2R)—N-(piperidin-4-ylmethyl)-2-(pyridin-3-yl)cyclopropanamine;

(1R,2S)—N-(piperidin-4-ylmethyl)-2-(pyridin-3-yl)cyclopropanamine;

(1S,2S)—N-(piperidin-4-ylmethyl)-2-(thiazol-5-yl)cyclopropanamine;

(1R,2R)—N-(piperidin-4-ylmethyl)-2-(thiazol-5-yl)cyclopropanamine;

(1S,2R)—N-(piperidin-4-ylmethyl)-2-(3'-(trifluoromethyl)-[1,1'-biphenyl]-4-yl)cyclopropanamine;

(1R,2S)—N-(piperidin-4-ylmethyl)-2-(3'-(trifluoromethyl)-[1,1'-biphenyl]-4-yl)cyclopropanamine;

(1S,2R)-2-(4-(benzyloxy)phenyl)-N-(piperidin-4-ylmethyl) cyclopropanamine;

(1R,2S)-2-(4-(benzyloxy)phenyl)-N-(piperidin-4-ylmethyl) cyclopropanamine;

(1S,2R)—N-(2-(piperidin-4-yl)ethyl)-2-(pyridin-3-yl)cyclopropanamine;

(1R,2S)—N-(2-(piperidin-4-yl)ethyl)-2-(pyridin-3-yl)cyclopropanamine;

(1S,2S)—N-(2-(piperidin-4-yl)ethyl)-2-(thiazol-5-yl)cyclopropanamine;

(1R,2R)—N-(2-(piperidin-4-yl)ethyl)-2-(thiazol-5-yl)cyclopropanamine;

(1S,2R)—N-(2-(piperidin-4-yl)ethyl)-2-(3'-(trifluoromethyl)-[1,1'-biphenyl]-4-yl)cyclopropanamine;

(1R,2S)—N-(2-(piperidin-4-yl)ethyl)-2-(3'-(trifluoromethyl)-[1,1'-biphenyl]-4-yl)cyclopropanamine;

(1S,2R)-2-(4-(benzyloxy)phenyl)-N-(2-(piperidin-4-yl) ethyl)cyclopropanamine;

(1R,2S)-2-(4-(benzyloxy)phenyl)-N-(2-(piperidin-4-yl) ethyl)cyclopropanamine;

(Trans)-2-phenyl-N-(pyrrolidin-3-ylmethyl)cyclopropanamine;

(Trans)-2-(4-((2-fluorobenzyl)oxy)phenyl)-N-(piperidin-4-ylmethyl)cyclopropanamine;

(Trans)-N-(azetidin-3-ylmethyl)-2-phenylcyclopropanamine;

(Trans)-2-(4-cyclopropylphenyl)-N-(piperidin-4-ylmethyl) cyclopropanamine;

(Trans)-N-(piperidin-4-ylmethyl)-2-(4-(pyridin-3-yl)phenyl)cyclopropanamine;

(Trans)-2-(4-(1H-pyrazol-5-yl)phenyl)-N-(piperidin-4-ylmethyl)cyclopropanamine;

(Trans)-2-(naphthalen-2-yl)-N-(piperidin-4-ylmethyl)cyclopropanamine;

2-methyl-2-phenyl-N-(piperidin-4-ylmethyl)cyclopropanamine;

(trans)-2-methyl-2-phenyl-N-(piperidin-4-ylmethyl)cyclopropanamine;

(trans)-2-(4-(benzyloxy)phenyl)-N-((1-methylpiperidin-4-yl)methyl)cyclopropanamine;

4-((4-((((1R,2S)-2-phenylcyclopropyl)amino)methyl)piperidin-1-yl)methyl)benzoic acid (GSK2879552);

1-((4-(methoxymethyl)-4-(((1R,2S)-2-phenylcyclopropylamine)methyl)piperidin-1-yl)methyl)cyclobutanecarboxylic acid;

N-[(2S)-5-{[(1R,2S)-2-(4-fluorophenyl)cyclopropyl] amino}-1-(4-methylpiperazin-1-yl)-1-oxopentan-2-yl]-4-(1H-1,2,3-triazol-1-yl)benzamide;

4-[2-(4-amino-piperidin-1-yl)-5-(3-fluoro-4-methoxy-phenyl)-1-methyl-6-oxo-1,6-dihydro-pyrimidin-4-yl]-2-fluorobenzonitrile;

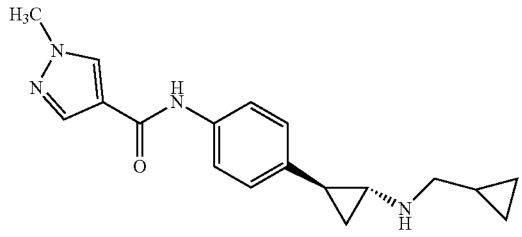
;

(T-3775440)

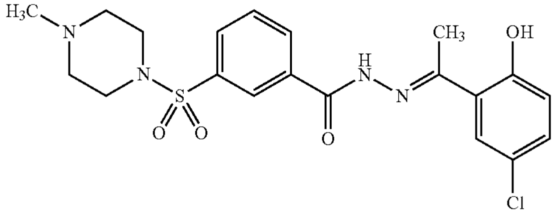
;

(seclidemstat)

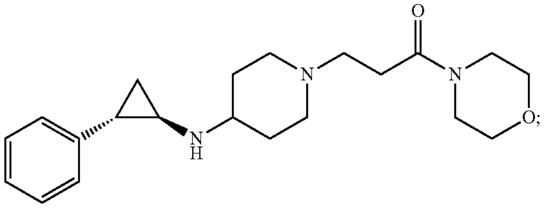

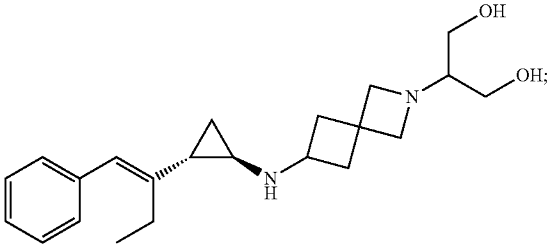

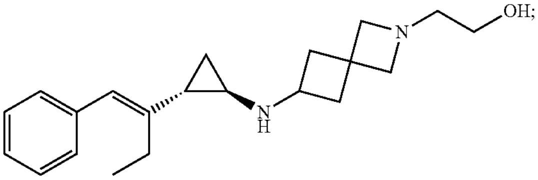
or

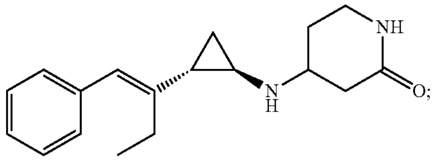 [SMILES: CC/C(=C\c1ccccc1)[C@@H]1C[C@H]1NC1CCNC(=O)C1]

including any optically active stereoisomer thereof, or a pharmaceutically acceptable salt or solvate thereof.

Pharmaceutical Formulations

While it is possible that a KDM1A inhibitor, for example vafidemstat, may be administered for use in therapy directly as such, it is typically administered in the form of a pharmaceutical composition, which comprises the compound as active pharmaceutical ingredient together with one or more pharmaceutically acceptable excipients or carriers.

Any reference to a KDM1A inhibitor throughout this specification includes a reference to the compound as such, i.e. the corresponding compound in non-salt form (e.g., as a free base) or in the form of any pharmaceutically acceptable salt or solvate thereof, as well as a reference to a pharmaceutical composition comprising said compound and one or more pharmaceutically acceptable excipients or carriers.

The KDM1A inhibitor may be administered by any means that accomplish the intended purpose. Examples include administration by the oral, parenteral (including e.g. intravenous, subcutaneous or intracerebral), or topical routes.

For oral delivery, the compound can be incorporated into a formulation that includes pharmaceutically acceptable carriers such as binders (e.g., gelatin, cellulose, gum tragacanth), excipients (e.g., starch, lactose), lubricants (e.g., magnesium stearate, silicon dioxide), disintegrating agents (e.g., alginate, Primogel, and corn starch), and sweetening or flavoring agents (e.g., glucose, sucrose, saccharin, methyl salicylate, and peppermint). The formulation can be orally delivered, e.g., in the form of enclosed gelatin capsules or compressed tablets. Capsules and tablets can be prepared by any conventional techniques. The capsules and tablets can also be coated with various coatings known in the art to modify the flavors, tastes, colors, and shapes of the capsules and tablets. In addition, liquid carriers such as fatty oil can also be included in capsules. Suitable oral formulations can also be in the form of suspension, syrup, chewing gum, wafer, elixir, and the like. If desired, conventional agents for modifying flavors, tastes, colors, and shapes of the special forms can also be included. In addition, for convenient administration by enteral feeding tube in patients unable to swallow, the active compounds can be dissolved in an acceptable lipophilic vegetable oil vehicle such as olive oil, corn oil and safflower oil.

The compound can also be administered parenterally in the form of solution or suspension, or in lyophilized form capable of conversion into a solution or suspension form before use. In such formulations, diluents or pharmaceutically acceptable carriers such as sterile water and physiological saline buffer can be used. Other conventional solvents, pH buffers, stabilizers, anti-bacteria agents, surfactants, and antioxidants can all be included. For example, useful components include sodium chloride, acetates, citrates or phosphates buffers, glycerin, dextrose, fixed oils, methyl parabens, polyethylene glycol, propylene glycol, sodium bisulfate, benzyl alcohol, ascorbic acid, and the like. The parenteral formulations can be stored in any conventional containers such as vials and ampoules.

For topical administration, the compound can be formulated into lotions, creams, ointments, gels, powders, pastes, sprays, suspensions, drops and aerosols. Thus, one or more thickening agents, humectants, and stabilizing agents can be included in the formulations. Examples of such agents include, but are not limited to, polyethylene glycol, sorbitol, xanthan gum, petrolatum, beeswax, or mineral oil, lanolin, squalene, and the like. A special form of topical administration is delivery by a transdermal patch. Methods for preparing transdermal patches are disclosed, e.g., in Brown, et al. (1988) *Ann. Rev. Med.* 39:221-229 which is incorporated herein by reference.

Subcutaneous implantation for sustained release of the compound may also be a suitable route of administration. This entails surgical procedures for implanting an active compound in any suitable formulation into a subcutaneous space, e.g., beneath the anterior abdominal wall. See, e.g., Wilson et al. (1984) *J. Clin. Psych.* 45:242-247. Hydrogels can be used as a carrier for the sustained release of active compounds. Hydrogels are generally known in the art. They are typically made by crosslinking high molecular weight biocompatible polymers into a network, which swells in water to form a gel like material. Preferably, hydrogels are biodegradable or biosorbable. For purposes of this invention, hydrogels made of polyethylene glycols, collagen, or poly(glycolic-co-L-lactic acid) may be useful. See, e.g., Phillips et al. (1984) *J. Pharmaceut. Sci.,* 73: 1718-1720.

The compound can also be conjugated to a water soluble non-immunogenic non-peptidic high molecular weight polymer to form a polymer conjugate. For example, the compound can be covalently linked to polyethylene glycol to form a conjugate. Typically, such a conjugate exhibits improved solubility, stability, and reduced toxicity and immunogenicity. Thus, when administered to a patient, the compound in the conjugate can have a longer half-life in the body, and exhibit better efficacy. See generally, Burnham (1994) *Am. J. Hosp. Pharm.* 15:210-218. PEGylated proteins are currently being used in protein replacement therapies and for other therapeutic uses. For example, PEGylated interferon (PEG-INTRON A®) is clinically used for treating Hepatitis B. PEGylated adenosine deaminase (ADAGEN®) is being used to treat severe combined immunodeficiency disease (SCIDS). PEGylated L-asparaginase (ONCAPSPAR®) is being used to treat acute lymphoblastic leukemia (ALL). It is preferred that the covalent linkage between the polymer and the active compound and/or the polymer itself is hydrolytically degradable under physiological conditions. Such conjugates known as "prodrugs" can readily release the active compound inside the body. Controlled release of an active compound can also be achieved by incorporating the active ingredient into microcapsules, nanocapsules, or hydrogels generally known in the art. Other pharmaceutically acceptable prodrugs of the compound include, but are not limited to, esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters.

Liposomes can also be used as carriers for the active compound. Liposomes are micelles made of various lipids such as cholesterol, phospholipids, fatty acids, and derivatives thereof. Various modified lipids can also be used. Liposomes can reduce the toxicity of the active compounds, and increase their stability. Methods for preparing liposomal suspensions containing active ingredients therein are generally known in the art. See, e.g., U.S. Pat. No. 4,522,811; Prescott, Ed., Methods in Cell Biology, Volume XIV, Academic Press, New York, N.Y. (1976).

The pharmaceutical compositions, like oral and parenteral compositions, can be formulated in unit dosage forms for ease of administration and uniformity of dosage. As used herein, "unit dosage forms" refers to physically discrete units suitable as unitary dosages for administration to subjects, each unit containing a predetermined quantity of active ingredient calculated to produce the desired therapeutic effect, in association with one or more suitable pharmaceutical carriers.

In therapeutic applications, pharmaceutical compositions are to be administered in a manner appropriate to the disease to be treated, as determined by a person skilled in the medical arts. An appropriate dose and suitable duration and frequency of administration will be determined by such factors as the condition of the patient, the type and severity of the disease, the particular form of the active ingredient, the method of administration, among others. In general, an appropriate dose and administration regimen provides the pharmaceutical composition in an amount sufficient to provide therapeutic benefit, for example an improved clinical outcome, such as more frequent complete or partial remissions, or longer disease-free and/or overall survival, or lessening of symptoms severity, or any other objectively identifiable improvement as noted by the clinician. Effective doses may generally be assessed or extrapolated using experimental models like dose-response curves derived from in vitro or animal model test systems, or from clinical trials.

The pharmaceutical compositions of the invention can be included in a container, pack or dispenser together with instructions for administration.

KDM1A inhibitors, such as vafidemstat, have been found to be orally active and to be effective in the treatment of BPD when administered orally, as also illustrated in Example 3. Accordingly, it is preferred that the KDM1A inhibitor (e.g., vafidemstat) is administered by the oral route for the treatment of BPD.

The present invention also embraces the use of KDM1A inhibitors, in which one or more atoms are replaced by a specific isotope of the corresponding atom. For example, the invention encompasses the use of a KDM1A inhibitor, in which one or more hydrogen atoms (or, e.g., all hydrogen atoms) are replaced by deuterium atoms (i.e., $^2H$; also referred to as "D"). Accordingly, the invention also embraces KDM1A inhibitors which are enriched in deuterium. Naturally occurring hydrogen is an isotopic mixture comprising about 99.98 mol-% hydrogen-1 ($^1H$) and about 0.0156 mol-% deuterium ($^2H$ or D). The content of deuterium in one or more hydrogen positions in a KDM1A inhibitor can be increased using deuteration techniques known in the art. For example, a KDM1A inhibitor or a reactant or precursor to be used in the synthesis of the KDM1A inhibitor can be subjected to an H/D exchange reaction using, e.g., heavy water ($D_2O$). Further suitable deuteration techniques are described in: Atzrodt J et al., *Bioorg Med Chem,* 20(18), 5658-5667, 2012; William J S et al., *Journal of Labelled Compounds and Radiopharmaceuticals,* 53(11-12), 635-644, 2010; Modvig A et al., *J Org Chem,* 79, 5861-5868, 2014. The content of deuterium can be determined, e.g., using mass spectrometry or NMR spectroscopy. Unless specifically indicated otherwise, it is preferred that the KDM1A inhibitor to be used in accordance with the present invention is not enriched in deuterium. Accordingly, the presence of naturally occurring hydrogen atoms or $^1H$ hydrogen atoms in the KDM1A inhibitor is preferred. In general, it is preferred that none of the atoms in the KDM1A inhibitor to be used in accordance with the invention are replaced by specific isotopes.

DEFINITIONS

Unless defined otherwise, all technical and scientific terms used herein have the same meaning as commonly understood by one of ordinary skill in the art to which this invention pertains.

The following definitions apply throughout the present specification and claims, unless specifically indicated otherwise.

A "patient" or "subject" for the purposes of the present invention includes both humans and other animals, particularly mammals. Thus, the methods and uses of the invention are applicable to both human therapy and veterinary applications. In a preferred aspect the subject or patient is a mammal, and in the most preferred aspect the subject or patient is a human (e.g. a male or female human; who may be an adult, e.g. a human aged 18 years or older, or a child, e.g. a human aged 17 years or younger).

The terms "treatment", "treating" and the like are used herein to generally mean obtaining a desired pharmacological and/or physiological effect. The effect may be prophylactic in terms of completely or partially preventing a disease (herein, BPD) or symptom thereof and/or may be therapeutic in terms of partially or completely curing or ameliorating a disease (i.e. BPD) and/or a symptom or adverse effect attributed to the disease or partially or completely halting the progression of a disease and/or a symptom or adverse effect attributed to the disease. The term "treatment" as used herein covers any treatment of a disease (i.e. BPD) in a patient and includes, without limitation, any one or more of the following: (a) preventing BPD in a patient which may be predisposed/at risk of developing BPD; (b) delaying the onset of BPD; (c) inhibiting BPD, i.e. arresting, delaying or slowing down its development/progression; or (d) relieving the BPD, i.e. causing (complete or partial) regression, correction or alleviation of BPD. The present invention specifically and distinctly relates to each one of these forms of treatment.

As used herein, the term "therapeutically effective amount" refers to the amount sufficient to produce a desired biological effect (e.g., a therapeutic effect) in a subject. Accordingly, a therapeutically effective amount of a compound may be an amount which is sufficient to treat a disease (i.e. BPD), and/or delay the onset or progression of the disease, and/or alleviate one or more symptoms of the disease, when administered to a subject suffering from or susceptible to that disease.

As used herein, the abbreviation "BPD" refers to borderline personality disorder.

As used herein, a "pharmaceutically acceptable salt" is intended to mean a salt that retains the biological effectiveness of the free acids and/or bases of the specified compound and that is not biologically or otherwise undesirable. A compound may possess a sufficiently acidic, a sufficiently basic, or both functional groups, and accordingly react with any of a number of inorganic or organic bases, and inorganic and organic acids, to form a pharmaceutically acceptable salt. Exemplary pharmaceutically acceptable salts include those salts prepared by reaction of a compound according to the invention, e.g. vafidemstat with a mineral or organic acid, such as hydrochlorides, hydrobromides, sulfates, pyrosulfates, bisulfates, sulfites, bisulfites, phosphates, monohydrophosphates, dihydrophosphates, metaphosphates, pyrophosphates, chlorides, bromides, iodides, nitrates, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, gamma-hydroxybutyrates, glycollates, tartrates, methane-sulfonates, ethanesulfonates, propanesulfonates, benzenesulfonates, toluenesulfonates, trifluoromethansulfonates, naphthalene-1-sulfonates, naphthalene-2-sulfonates, mandelates, pyruvates, stearates, ascorbates, or salicylates. When a compound carries an acidic moiety, suitable pharmaceutically acceptable salts thereof may include alkali metal salts, e.g. sodium or potassium salts; alkaline earth metal salts, e.g. calcium or magnesium salts; and salts formed with suitable organic ligands such as ammonia, alkylamines, hydroxyalkylamines, lysine, arginine, N-methylglucamine, procaine and the like. Pharmaceutically acceptable salts are well known in the art.

As used herein, a "pharmaceutically acceptable solvate" refers to a complex of variable stoichiometry formed by a solute and a pharmaceutically acceptable solvent such as water, ethanol and the like. A complex with water is known as a hydrate. It is to be understood that the invention encompasses pharmaceutically acceptable solvates of any KDM1A inhibitors in non-salt form and also in the form of a pharmaceutically acceptable salt thereof.

As used herein, a "pharmaceutically acceptable carrier" or "pharmaceutically acceptable excipient" refers to non-API (API refers to Active Pharmaceutical Ingredient) substances such as disintegrators, binders, fillers, and lubricants used in formulating pharmaceutical products. They are generally safe for administering to humans according to established governmental standards, including those promulgated by the United States Food and Drug Administration and/or the European Medicines Agency. Pharmaceutically acceptable carriers or excipients are well known to those skilled in the art.

As used herein, a "small molecule" refers to an organic compound with a molecular weight below 900 daltons, preferably below 500 daltons. The molecular weight is the mass of a molecule and is calculated as the sum of the atomic weights of each constituent element multiplied by the number of atoms of that element in the molecular formula.

As used herein, the term "comprising" (or "comprise", "comprises", "contain", "contains", or "containing"), unless explicitly indicated otherwise or contradicted by context, has the meaning of "containing, inter alia", i.e., "containing, among further optional elements, . . . ". In addition thereto, this term also includes the narrower meanings of "consisting essentially of" and "consisting of". For example, the term "A comprising B and C" has the meaning of "A containing, inter alia, B and C", wherein A may contain further optional elements (e.g., "A containing B, C and D" would also be encompassed), but this term also includes the meaning of "A consisting essentially of B and C" and the meaning of "A consisting of B and C" (i.e., no other components than B and C are comprised in A).

As used herein, unless explicitly indicated otherwise or contradicted by context, the terms "a" "an" and "the" are used interchangeably with "one or more" and "at least one". Thus, for example, a composition comprising "a" KDM1A inhibitor can be interpreted as referring to a composition comprising "one or more" KDM1A inhibitors.

EXAMPLES

The following examples illustrate various aspects of the invention. The examples should, of course, be understood to be merely illustrative of only certain embodiments of the invention and not to constitute limitations upon the scope of the invention. Results are also presented and described in the Figures and Figure legends.

Example 1: KDM1A Inhibitor

Vafidemstat is the compound 5-((((1R,2S)-2-(4-(benzyloxy)phenyl)cyclopropyl)amino)methyl)-1,3,4-oxadiazol-2-amine, also known as (−) 5-((((trans)-2-(4-(benzyloxy)phenyl)cyclopropyl)amino)methyl)-1,3,4-oxadiazol-2-amine, (41R,42S)-6-oxa-3-aza-1(2)-[1,3,4]oxadiazola-5(1,4),8(1)-dibenzena-4(1,2)-cyclopropanaoctaphan-15-amine or ORY-2001, and whose chemical structure is shown below.

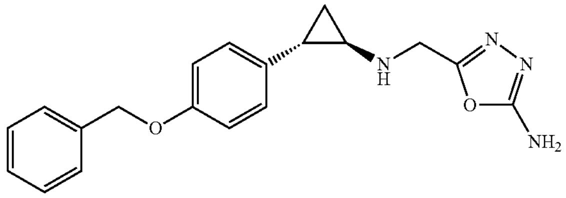 [SMILES: Nc1nnc(CN[C@@H]2C[C@H]2c2ccc(OCc3ccccc3)cc2)o1]

This compound can be obtained as disclosed in WO2012/013728.

Example 2: In Vitro KDM1A Inhibition Assay

The inhibitory activity of a compound against KDM1A can be determined using the method described below. Human recombinant KDM1A protein (GenBank accession no. NM_015013, amino acids 158-end with N-terminal GST tag, MW: 103 kDa) was used.

Serial 3-fold dilutions of a test compound ranged between 30 M and 1 nM were pre-incubated for 15 min with human recombinant KDM1A enzyme (BPS Bioscience, Ref. 50100) on ice in the assay buffer (50 mM sodium phosphate pH 7.4). Each concentration of inhibitor was tested in duplicate. The enzymatic reaction was initiated by the addition of dimethyl H3K4 peptide substrate (Anaspec, Ref. 63677), at the app$K_M$ of KDM1A. After 30 min of incubation at 37° C. Amplex Red reagent and the horseradish peroxidase (HRP) solution were added to detect $H_2O_2$ formed in the enzymatic reaction, following the recommendations provided by the supplier (Invitrogen). The mix was incubated for 5 min at room temperature in the dark and the conversion of the Amplex Red reagent to the highly fluorescent resorufin was analyzed using an Infinite F200 Tecan fluorescence microplate reader (λexcitation=540 nm, λemission=590 nm). The maximum demethylase activity of KDM1A was obtained in the absence of inhibitor and corrected for background fluorescence in the absence of KDM1A. The $IC_{50}$ value for each inhibitor was calculated with GraphPad Prism5 Software from a minimum of two independent experiments.

Vafidemstat is a KDM1A inhibitor, as shown by a mean $IC_{50}$ value of 101±40 nM obtained in the KDM1A assay described herein.

Example 3: Evaluation of the Effect of KDM1A Inhibitors to Treat BPD in Humans As part of a Phase IIa clinical trial (REIMAGINE trial, EudraCT number 2018-002140-88) to evaluate the safety, tolerability and efficacy of the KDM1A inhibitor vafidemstat to treat aggression in adult population in patients with different CNS disorders, a cohort of BPD patients was recruited and treated with vafidemstat for 8 weeks. A summary of the protocol of this clinical trial and results obtained in the BPD cohort are provided below.

3.1 Clinical Trial Design

Reimagine is a unicenter, open-label, 1-arm, 8-week clinical study to evaluate the efficacy, safety and tolerability of vafidemstat in aggression in adult population with Alzheimer's Disease (AD), Lewy Body Dementia (LBD), Adult attention Deficit Hyperactivity Disorder (ADHD), Borderline Personality Disorder (BPD) and Autism Spectrum Disorder (ASD). Six patients to be recruited per disorder.

Main objective of the trial: To evaluate the safety and tolerability of vafidemstat in adult population with Alzheimer's Disease (AD), Lewy Body Dementia (LBD), Adult attention deficit hyperactivity disorder (ADHD), Borderline Personality Disorder (BPD), Autism Spectrum Disorder (ASD)

Secondary objectives of the trial: To investigate the efficacy of vafidemstat in aggression in adult population with Alzheimer's Disease (AD), Lewy Body Dementia (LBD), Adult attention deficit hyperactivity disorder (ADHD), Borderline Personality Disorder (BPD), Autism Spectrum Disorder (ASD)

Main inclusion criteria:
- age 18-85
- current diagnosis for AD, LBD, ADHD, BPD or ASD according to DSM-5 criteria
- significant or persistent agitation or aggression that was disruptive to patient's daily living or put the patient in harm's way for at least 3 days per week for at least 4 weeks prior to screening visit Treatment: All patients received vafidemstat (as free base) at a dose of 1.2 mg/day, administered orally as a single capsule, in a 5 days on/2 days off schedule, during 8 weeks.

3.2 BPD Cohort

Six BPD patients were recruited, but there was one drop-out, and therefore the results as described herein correspond to the 5 BPD subjects eligible for analysis. A summary of the patients recruited in this BPD cohort (demographic data at baseline) can be found in Table 1.

TABLE 1

| Demographic data BPD patients | | |
|---|---|---|
| n° of patients | | 6 |
| Sex | Male | 0 (0%) |
| | Female | 6 (100%) |
| Age | Median (years) | 37.33 |
| | (Min , Max ) | (25/46) |
| Race | Caucasian | 6 (100%) |
| Weight | Median (Kg) | 60.72 |
| | (Min , Max ) | (52.7/89.8) |
| Height | Median (cm) | 164.37 |
| | (Min , Max ) | (162/172) |
| BMI | Median | 22.51 |
| | (Min , Max ) | (19.39/33.39) |

3.3 Efficacy Assessments in the BPD Cohort

Assessment of efficacy of treatment in BPD patients was performed using a validated scale specific for BPD, the Borderline Personality Disorder Checklist (BPDCL). The BPDCL is an instrument specifically designed to evaluate the subjective burden of BPD in the last month and also to rate BPD changes after therapeutic intervention. Originally developed in Dutch, the BPDCL has been subsequently translated into English, Spanish and other languages, and has been applied to clinical and non-clinical samples. The BPDCL has been shown to exhibit adequate psychometric properties and is currently regarded as the most reliable scale to assess efficacy of treatments aimed at BPD.

The BPDCL is a 47-item self-report questionnaire; the items were based on DSM-IV BPD criteria, the literature describing the BPD manifestations, and clinical observations. Items are rated on a 5-point Likert scale, ranging from "not at all" to "extremely", indicating the extent to which the respondent was troubled by the 47 different BPD complaints during the last month. The 47 items in the BPDCL can be clustered together into the following 9 BPD domains:

1) Abandonment
2) Relationships
3) Identity disturbance
4) Impulsivity
5) (Para)suicide
6) Affective instability
7) Emptiness
8) Anger control
9) Dissociation One can use the total sum score on the BPDCL (BPDCL Total Score) as an overall index of the subjective burden caused by BPD symptoms, or one can use sum scores for one or more of the separate BPD domains. The BPDCL was performed on day 1 (Visit 1), which corresponds to baseline (i.e. prior to start of treatment with vafidemstat), and on week 8 of treatment with vafidemstat (Visit 7). Efficacy assessments were always measured prior to treatment administration on the corresponding visit day.

Efficacy evaluation was performed by assessing the change from baseline (visit 1) to week 8 (visit 7) of the aggression-related BPDCL domains combined score (i.e. the score resulting from the combination of the scores of the BPDCL domains related to aggressive behavior, namely: anger control, impulsivity and (para)suicide), the BPDCL Total score, as well as the non-aggression-related BPDCL domains combined score (i.e. the score resulting from the combination of all other BPDCL domain scores, namely: abandonment, relationships, identity disturbance, affective instability, emptiness and dissociation).

Statistical analysis was performed using paired one-tail t-test analysis to compare Visit 1 with Visit 7 values.

3.4 Results

Treatment with vafidemstat in the BPD patients was safe and well tolerated, without significant adverse events. Treatment of BPD patients with vafidemstat for 8 weeks produced a significant improvement in aggression, as shown by a statistically significant reduction of the aggression-related BPDCL domains combined score (as detailed above in Example 3.3) from visit 1 to visit 7, as shown in FIG. 1 ($p=0.0029$).

Unexpectedly, not only the aggression-related combined score, but also the BPDCL Total Score and the non-aggression-related BPDCL domains combined score all showed a statistically significant reduction after 2 months of treatment with vafidemstat, as shown in FIG. 2 (Total BPDCL Score, $p=0.0048$) and FIG. 3 (non-aggression-related BPDCL domain combined score, $p=0.0234$).

The significant improvements observed in the BPDCL Total Score and in the non-aggression combined score via treatment of BPD patients with vafidemstat show that KDM1A inhibitors such as vafidemstat have additional therapeutic effects in BPD patients beyond the treatment of aggression.

Summarized, the data and results obtained in Example 3 support the finding that KDM1A inhibitors, particularly vafidemstat, are useful for the treatment of BPD, including the treatment of BPD core features or BPD symptoms unrelated to aggression.

Using the protocol described herein in Example 3, the therapeutic effects of other KDM1A inhibitors as a treatment for BPD can be verified.

All publications, patents and patent applications cited herein are hereby incorporated herein by reference in their entireties.

The publications, patents and patent applications mentioned in the specification are provided solely for their disclosure prior to the filing date of the present application.

Nothing herein is to be construed as an admission that they are prior art to the instant application.

While the invention has been described in connection with specific embodiments thereof, it will be understood that it is capable of further modifications and this application is intended to cover any variations, uses or adaptations of the invention following, in general, the principles of the invention and including such departures from the present disclosure as come within known or customary practice within the art to which the invention pertains and as may be applied to the essential features hereinbefore set forth and as follows in the appended claims.

The invention claimed is:

1. A method for treating one or more non-aggressive symptoms of borderline personality disorder in a patient having borderline personality disorder, comprising administering to the patient a therapeutically effective amount of a KDM1A inhibitor.

2. The method according to claim 1, wherein the patient to be treated is a human.

3. The method according to claim 1, wherein the KDM1A inhibitor is 5-((((1R,2S)-2-(4-(benzyloxy)phenyl)cyclopropyl)amino)methyl)-1,3,4-oxadiazol-2-amine, or a pharmaceutically acceptable salt or solvate thereof.

4. The method according to claim 1, wherein the KDM1A inhibitor is 5-((((1R,2S)-2-(4-(benzyloxy)phenyl)cyclopropyl)amino)methyl)-1,3,4-oxadiazol-2-amine.

5. The method according to claim 1, wherein the method comprises orally administering the KDM1A inhibitor.

6. The method according to claim 2, wherein the KDM1A inhibitor is 5-((((1R,2S)-2-(4-(benzyloxy)phenyl)cyclopropyl)amino)methyl)-1,3,4-oxadiazol-2-amine, or a pharmaceutically acceptable salt or solvate thereof.

7. The method according to claim 6, wherein the method comprises orally administering the KDM1A inhibitor.

8. The method according to claim 2, wherein the KDM1A inhibitor is 5-((((1R,2S)-2-(4-(benzyloxy)phenyl)cyclopropyl)amino)methyl)-1,3,4-oxadiazol-2-amine.

9. The method according to claim 8, wherein the method comprises orally administering the KDM1A inhibitor.

10. A method for treating one or more non-aggressive symptoms of borderline personality disorder in a human patient having borderline personality disorder, comprising administering to the patient a therapeutically effective amount of 5-((((1R,2S)-2-(4-(benzyloxy)phenyl)cyclopropyl)amino)methyl)-1,3,4-oxadiazol-2-amine or a pharmaceutically acceptable salt or solvate thereof.

11. A method for treating one or more non-aggressive symptoms of borderline personality disorder in a human patient having borderline personality disorder, comprising orally administering to the patient a therapeutically effective amount of 5-((((1R,2S)-2-(4-(benzyloxy)phenyl)cyclopropyl)amino)methyl)-1,3,4-oxadiazol-2-amine.

* * * * *